(12) United States Patent
O'Neill et al.

(10) Patent No.: US 8,221,992 B2
(45) Date of Patent: Jul. 17, 2012

(54) ASSAYS FOR DETERMINING COMPOUNDS WHICH MODULATE TRAM PHOSPHORYLATION

(75) Inventors: Luke Anthony O'Neill, Dublin (IE); Anne McGettrick, Dublin (IE)

(73) Assignee: Opsona Therapeutics Limited, Dublin (IE)

( * ) Notice: Subject to any disclaimer, the term of this patent is extended or adjusted under 35 U.S.C. 154(b) by 561 days.

(21) Appl. No.: 11/910,518

(22) PCT Filed: Apr. 3, 2006

(86) PCT No.: PCT/IE2006/000023
§ 371 (c)(1),
(2), (4) Date: Jun. 13, 2008

(87) PCT Pub. No.: WO2006/106492
PCT Pub. Date: Oct. 12, 2006

(65) Prior Publication Data
US 2009/0123482 A1    May 14, 2009

Related U.S. Application Data

(60) Provisional application No. 60/674,828, filed on Apr. 26, 2005.

(30) Foreign Application Priority Data

Apr. 2, 2005    (GB) .................................. 0506768.1
Oct. 20, 2005   (GB) .................................. 0521325.1

(51) Int. Cl.
    *G01N 33/567*    (2006.01)
(52) U.S. Cl. .......... 435/7.21; 435/7.2; 435/7.24; 436/63
(58) Field of Classification Search ........................ None
See application file for complete search history.

(56) References Cited

FOREIGN PATENT DOCUMENTS

JP    2005021042    1/2005
WO   WO2005/030269  9/2004

OTHER PUBLICATIONS

International Search Report for PCT/IE2006/000023 dated Nov. 7, 2006.
Yamamoto et al, Nature Immunology, vol. 4, No. 11, Nov. 2003, pp. 1144-1150.
Aksoy et al, Eur. J. Immunol., vol. 32, 2002, pp. 3040-3049.
Castrillo et al, J. Exp. Med., vol. 194, No. 9, Nov. 5, 2001, pp. 1231-1242.
Cuschieri et al, Journal of Surgical Research 121, 2004, pp. 76-83.
McGettrick et al, PNAS, vol. 103, No. 24, Jun. 13, 2006, pp. 9196-9201.
Rowe et al, PNAS, vol. 103, No. 16, Apr. 18, 2006, pp. 6299-6304.
UK Search Report for Application No. GB0506768.1 dated Jul. 11, 2008.
Oshiumi et al, The Journal of Biological Chemistry, vol. 278, No. 50, Dec. 12, 2003, pp. 49751-49762.
Bin et al, The Journal of Biological Chemistry, vol. 278, No. 27, Jul. 4, 2003, pp. 24526-24532.
Takeda, Curr. Med. Chem.—Anti-inflammatory & Anti-Allergy Agents, No. 4, 2005, pp. 3-11.
Takeda et al, International Immunology, vol. 17, No. 1, 2005, pp. 1-14.
Hoebe et al, Journal of Endotocin Research, vol. 10, No. 2, Jan. 8, 2004, pp. 130-136.
Dunne and O'Neill, "The Interleukin-1 Receptor/Toll-Like Receptor Superfamily," Sci. STKE, re3 (2003), 17 pages.
Fitzgerald et al., "Mal (MyD88-adapter-like) is required for Toll-like Receptor-4 signal transduction," J. Nature, 143:78-83 (2001).
Fitzgerald et al., "LPS-TLR4 Signaling to IRF-3/7 and NF-.B Involves the Toll Adapters TRAM and TRIF," J. Exp. Med., 198:1043-1055 (2003).
Horng and Barton, "TIRAP an adaptor molecule in the Toll signalling pathway," Nat. Immunol. 2:835-841 (2001).
Horng et al., "The adaptor molecule TIRAP provides signalling specificity for Toll-like receptors," Nature, 420:329-333 (2002).
Janeway and Medzhitov, "Innate Immune Recognition," Annu. Rev. Immunol., 20:197-216 (2002).
McGettrick and O'Neill, "The expanding family of MyD88-like adaptors in Toll-like receptor signal transduction," Mol. Immunol., 41:577-582 (2004).
Oshiumi et al., "TICAM-I, an adaptor molecule that participates in Toll-like receptor 3-mediated interferon-β induction," Nat. Immunol., 4:161-167 (2003).
Takeuchi et al., ". . . R-Stereoisomer of the Mycoplamal Lipopeptide Macrophage-Activating Lipopeptide-2 Activates Immune Cells . . . ," J. Immunol., 164:554-557 (2000).
Yamamoto et al., "A Novel Toll/IL-1 Receptor Domain-Containing Adapter that Preferentially Activates the IFN-β Promoter . . . ," J. Immunol., 169: 6668-6672 (2002).
Yamamoto et al., Role of Adaptor TRIF in the MyD88-Independent Toll-Like Receptor Signaling Pathway, Science, 301:640-643 (2003).
Yamamoto et al., "TRAM is specifically involved in the Toll-like receptor 4-mediated MyD88-independent signaling pathway," Nature Immunol. (2003) 4(11):1144-1150.

*Primary Examiner* — Daniel C Gamett
(74) *Attorney, Agent, or Firm* — Lando & Anastasi, LLP

(57) ABSTRACT

Disclosed are assays for the determination and quantification of the phosphorylation of TRAM (Trif-related adaptor molecule). TRAM is rapidly phosphorylated upon LPS stimulation by protein kinase C epsilon (PKCε) and that this phosphorylation is vital for TRAM to function normally. Assays suitable for detecting the state of phosphorylation of TRAM have utility in identifying compounds which have activity in modulating TRAM. Further disclosed are compounds which have utility in modulating the phosphorylation of TRAM to modulate signalling mediating by the Toll Like Receptor 4 (TLR4) receptor.

19 Claims, 14 Drawing Sheets

Figure 1

(a) TRAM-N 5' GGGGATCCATGGGTATCGGGAAGTCTAAAATAAATTCC 3' (SEQ ID NO: 2)
TRAM-C 5' GGGAATTCTCAGGCAATAAATTGTCTTTGTACCATATTTCTTG 3' (SEQ ID NO: 3)

(b) 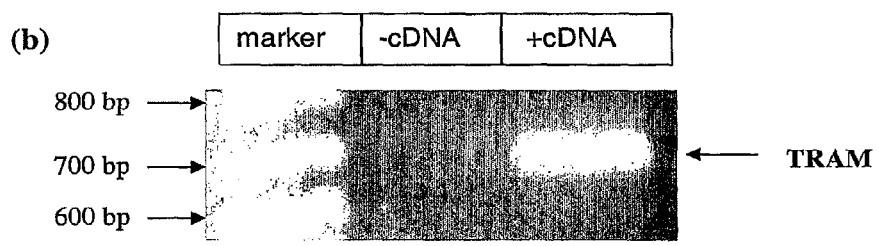

(c) 4Ser      tatcgggaaggctaaaataaatgcctgccctcttgctctcgcttggggtaaaa (SEQ ID NO: 4)
    4SerRev   ttttaccccaagcgagagcaagagggcaggcatttattttagccttcccgata (SEQ ID NO: 5)

Ser16     ataaattcctgccctctttctctcgcttggggtaaaaggcacagt (SEQ ID NO: 6)
    Ser 16rev actgtgccttttaccccaagcgagagaaagagggcaggaatttat (SEQ ID NO: 7)

Figure 2
(a)
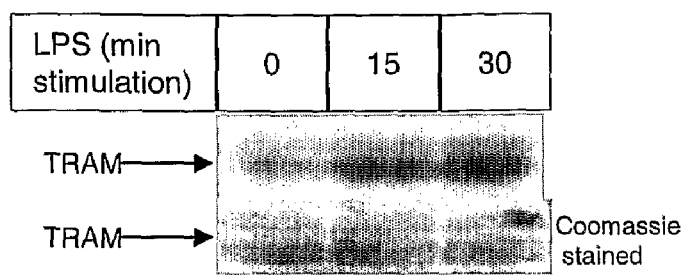
(b)
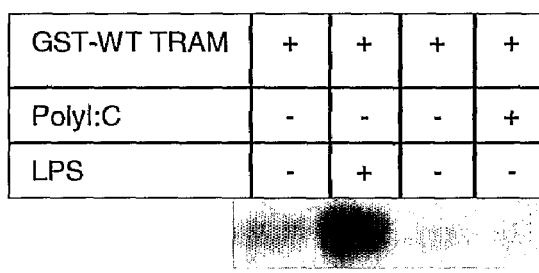
(c)
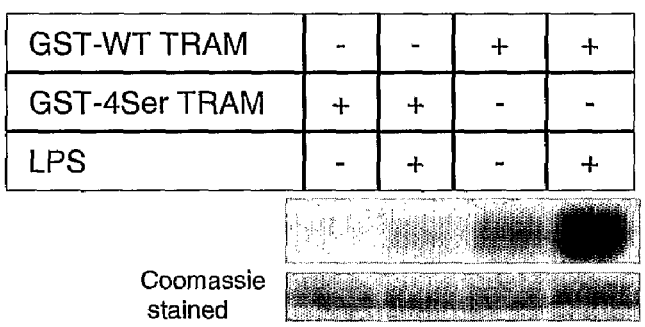
(d)
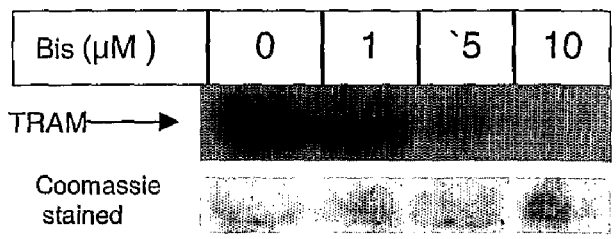

Figure 2
(e)
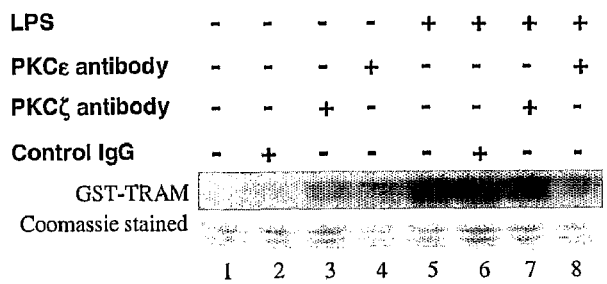
(f)
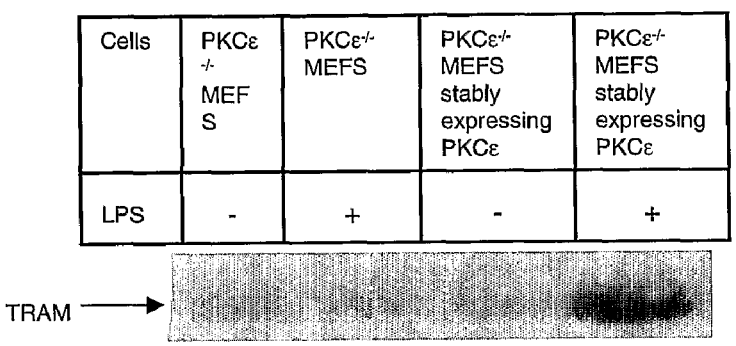
(g)
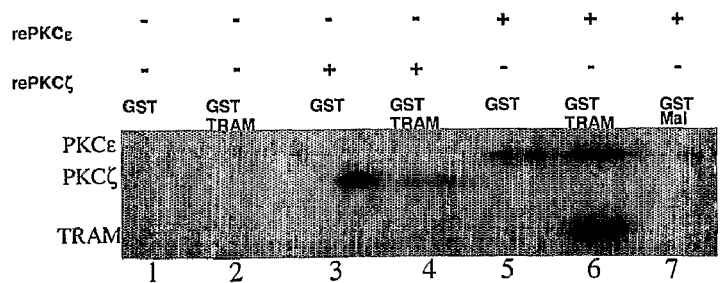

Figure 3
(a)
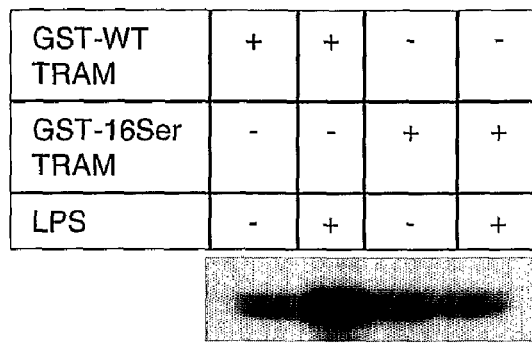
(b)
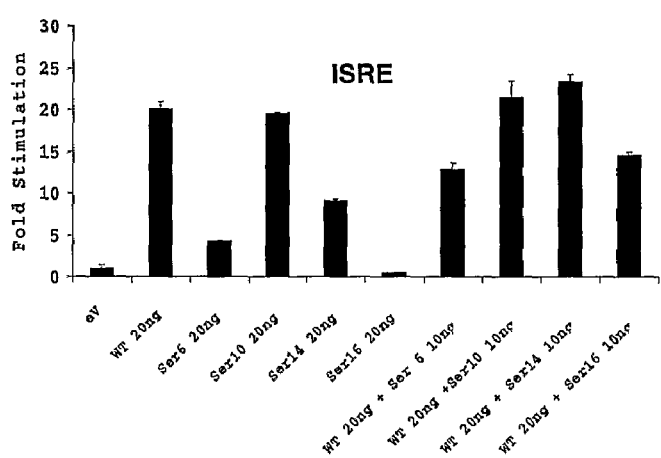
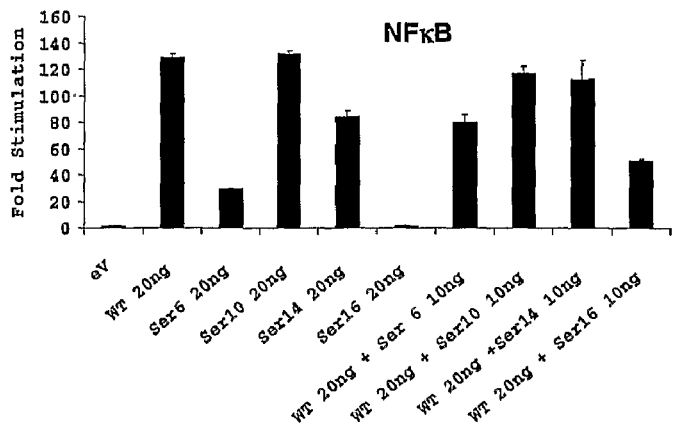

Figure 3
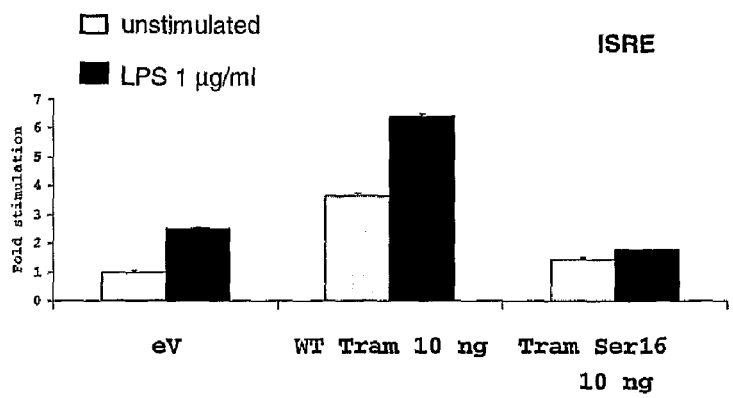
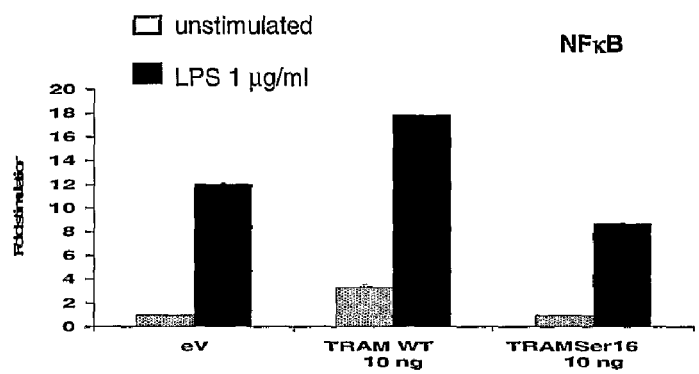
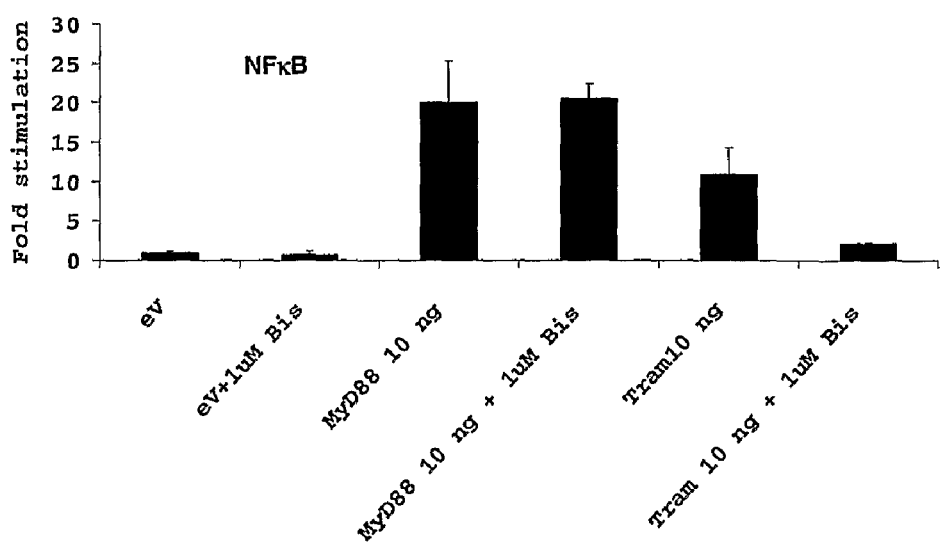

Figure 4
(a)
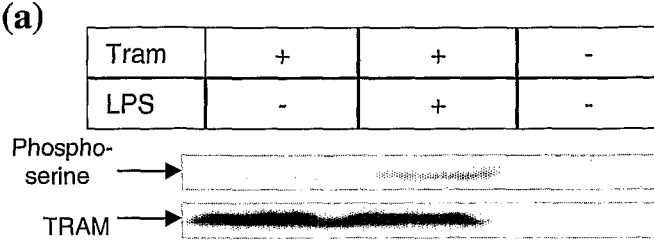
(b)
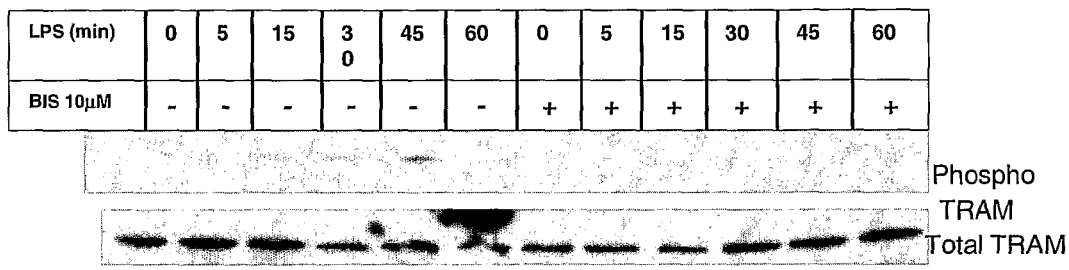
(c)
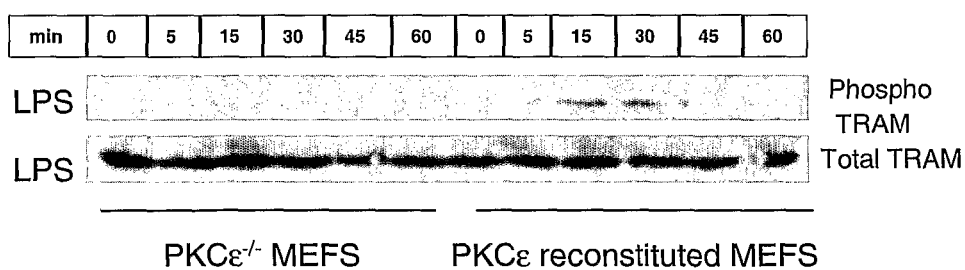
(d)
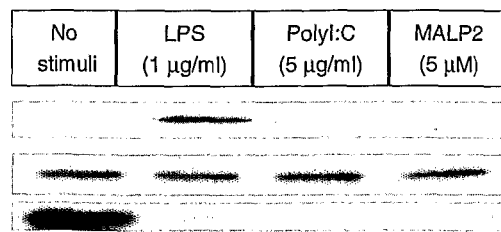

Figure 5 (b)
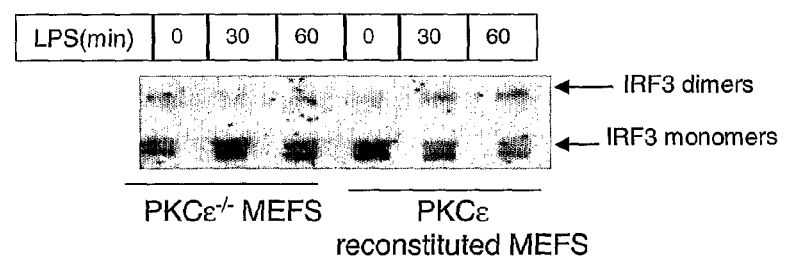
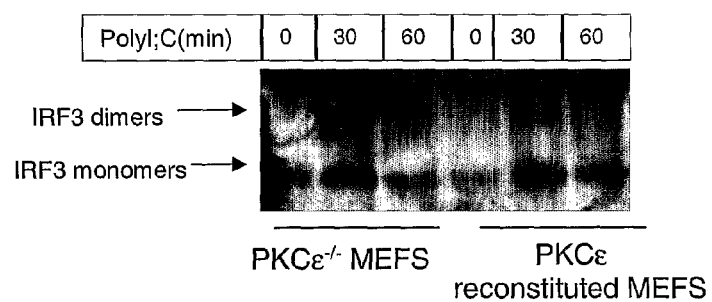

Figure 5 (c)
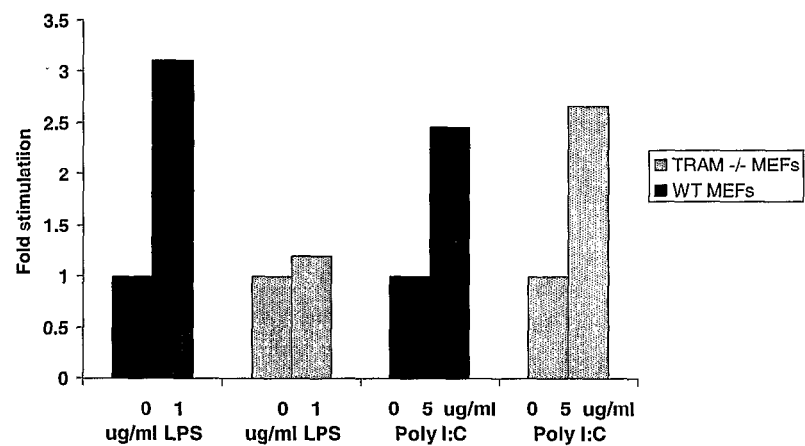
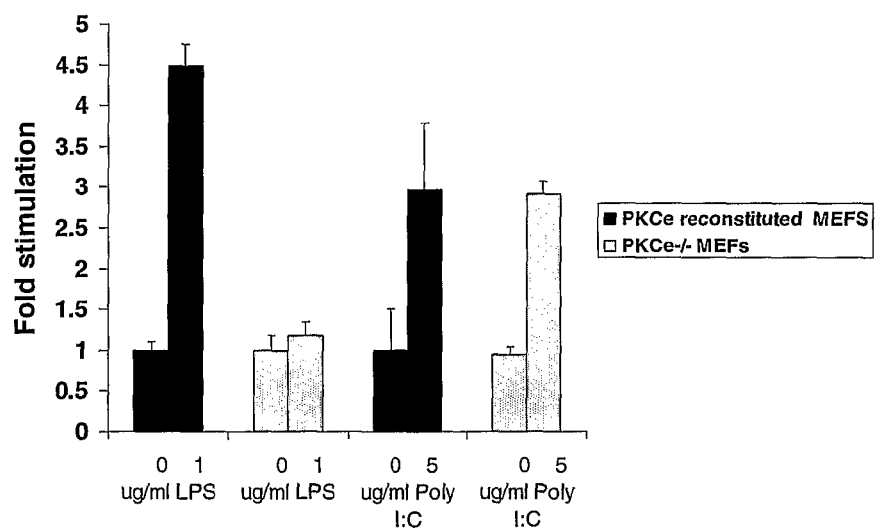

Figure 5 (d)
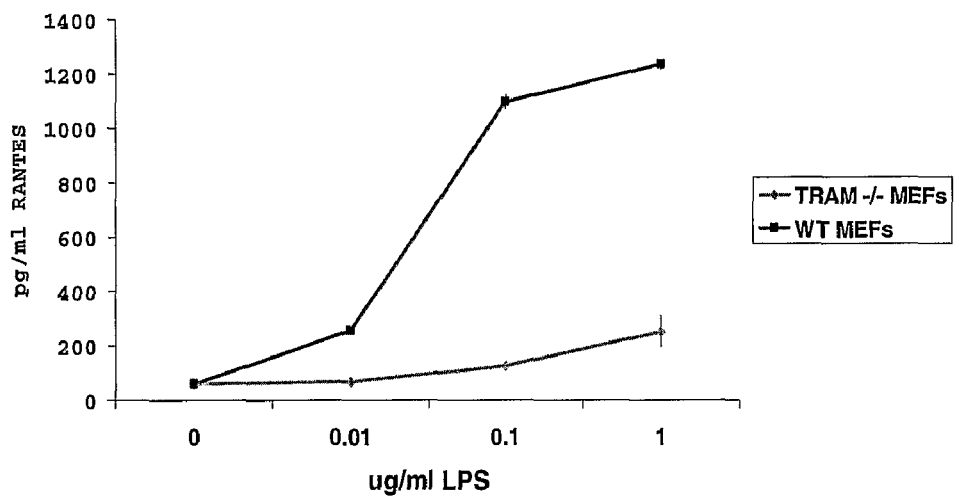
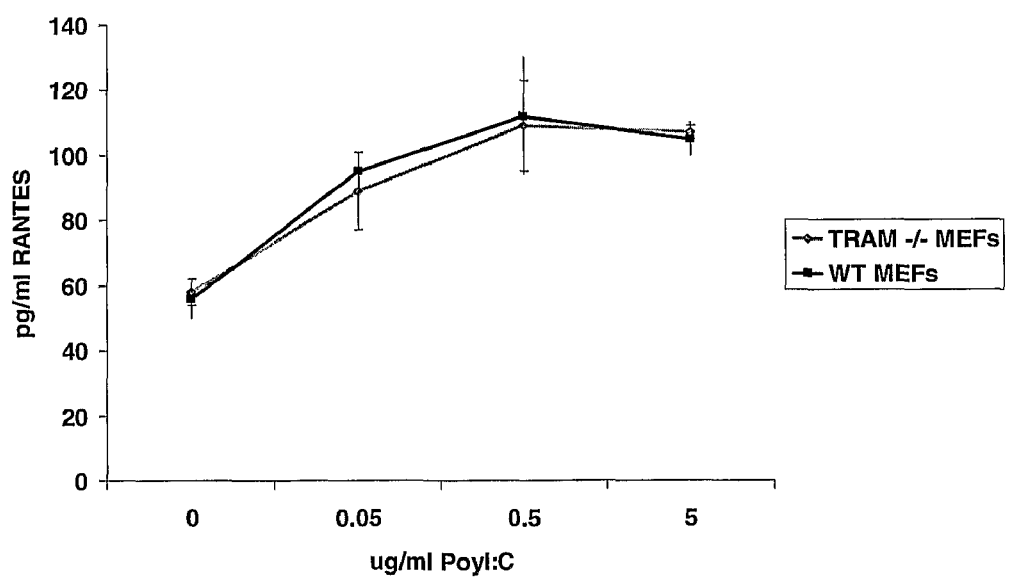

Figure 5 (e)
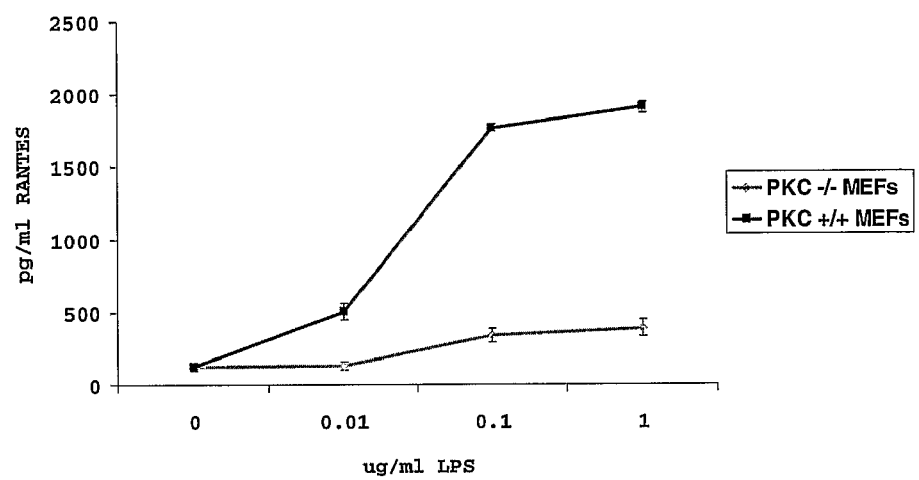
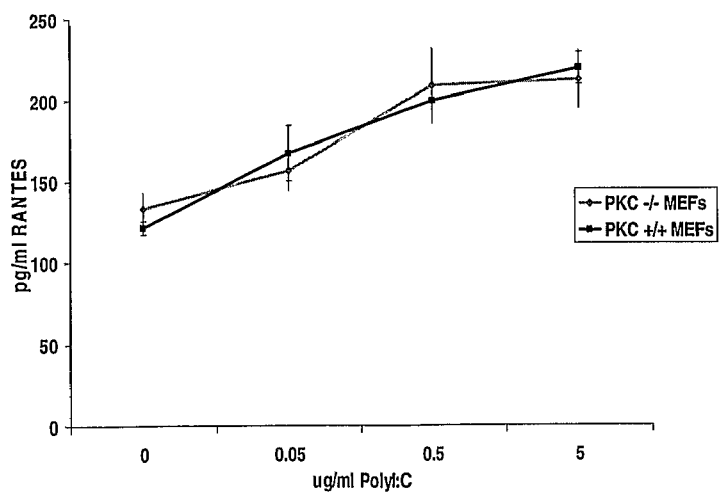

Figure 6
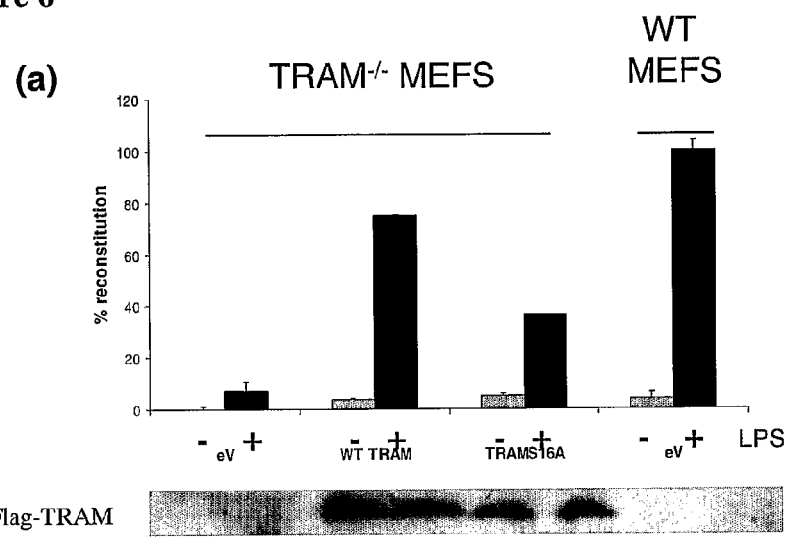
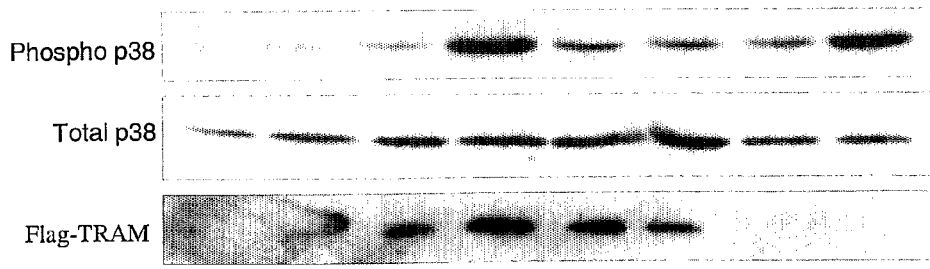

Figure 8
(a)
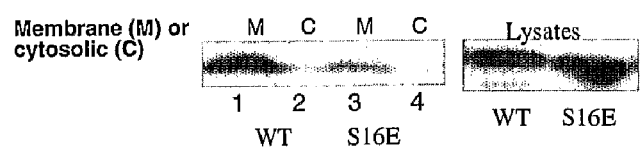
(b)
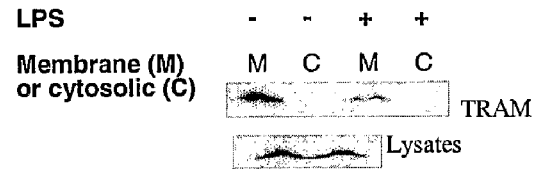
(c)
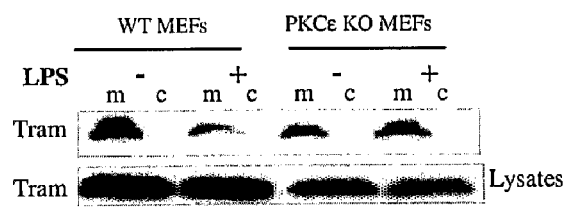

SEQUENCE LISTING

```
<160> NUMBER OF SEQ ID NOS: 7

<210> SEQ ID NO 1
<211> LENGTH: 18
<212> TYPE: PRT
<213> ORGANISM: Homo sapiens

<400> SEQUENCE: 1

Met Gly Ile Gly Lys Ser Lys Ile Asn Ser Cys Pro Leu Ser Leu Ser
1               5                   10                  15

Trp Gly

<210> SEQ ID NO 2
<211> LENGTH: 38
<212> TYPE: DNA
<213> ORGANISM: Artificial
<220> FEATURE:
<223> OTHER INFORMATION: primer TRAM-N 5'

<400> SEQUENCE: 2
ggggatccat gggtatcggg aagtctaaaa taaattcc                              38

<210> SEQ ID NO 3
<211> LENGTH: 43
<212> TYPE: DNA
<213> ORGANISM: Artificial
<220> FEATURE:
<223> OTHER INFORMATION: primer TRAM-C 5'
```

-continued

```
<400> SEQUENCE: 3
gggaattctc aggcaataaa ttgtctttgt accatatttc ttg                    43

<210> SEQ ID NO 4
<211> LENGTH: 53
<212> TYPE: DNA
<213> ORGANISM: Artificial
<220> FEATURE:
<223> OTHER INFORMATION: primer 4Ser

<400> SEQUENCE: 4
tatcgggaag gctaaaataa atgcctgccc tcttgctctc gcttggggta aaa         53

<210> SEQ ID NO 5
<211> LENGTH: 53
<212> TYPE: DNA
<213> ORGANISM: Artificial
<220> FEATURE:
<223> OTHER INFORMATION: primer 4SerRev

<400> SEQUENCE: 5
ttttacccca agcgagagca agagggcagg catttatttt agccttcccg ata         53

<210> SEQ ID NO 6
<211> LENGTH: 45
<212> TYPE: DNA
<213> ORGANISM: Artificial
<220> FEATURE:
<223> OTHER INFORMATION: primer Ser16

<400> SEQUENCE: 6
ataaattcct gccctctttc tctcgcttgg ggtaaaaggc acagt                  45

<210> SEQ ID NO 7
<211> LENGTH: 45
<212> TYPE: DNA
<213> ORGANISM: Artificial
<220> FEATURE:
<223> OTHER INFORMATION: primer Ser 16rev

<400> SEQUENCE: 7
actgtgcctt ttaccccaag cgagagaaag agggcaggaa tttat                  45
```

ASSAYS FOR DETERMINING COMPOUNDS WHICH MODULATE TRAM PHOSPHORYLATION

CROSS-REFERENCE TO RELATED APPLICATIONS

This application is a national stage application claiming priority under 35 U.S.C. § 371 to PCT Application Ser. No. PCT/IE2006/000023, published as WO 2006/106492, with an international filing date of Apr. 3, 2006, the contents of which application is hereby incorporated by reference herein entirety.

FIELD OF THE INVENTION

The present invention relates to novel assays for the determination and quantification of the phosphorylation of TRAM (Trif-related adaptor molecule). The assays may, in particular, be used to monitor the activation of Toll Like Receptor 4 (TLR4), with such a assays having utility in the identification of modulators of the activity thereof. A further aspect of the invention provides an assay for use in determining molecules which block, inhibit or competitively inhibit the phosphorylation of TRAM by protein kinase C epsilon.

BACKGROUND TO THE INVENTION

The Toll-like receptor (TLR) superfamily plays a central role in the recognition of invading pathogens and the initiation of an immune response. Ten human TLRs have been identified to date. Each recognises a distinct pathogen-associated molecular pattern (PAMP) leading to the activation of a signalling cascade, which in turn activates the transcription factor NF-κB and also the mitogen-activated protein kinases (MAPKs), p38, c-jun, N terminal kinase (JNK) and p42/44 (reviewed in ref 1 and 2). TLR3 and TLR4 also activate another pathway culminating in the activation of the transcription factor, IFN-regulated factor-3 (IRF3), which binds to the interferon-sensitive response element (ISRE), inducing a subset of genes including IFN-β (3). The TLRs are members of a larger superfamily, called the interleukin-1 receptor (IL-1R)/TLR superfamily, that also contains the IL-1R1 subgroup and the TIR domain-containing adaptor subgroup. All three subgroups possess a cytoplasmic Toll/IL-1 receptor (TIR) domain, which is essential for signalling. The TLRs possess extracellular leucine rich repeats, while the IL-1R1 subgroup have extracellular immunoglobin domains. The adaptor molecules are cytoplasmic and contain no extracellular region.

As mentioned above, each TLR recognises a different PAMP. The first TLR to be discovered was TLR4 and it is essential for the recognition of gram-negative bacterial lipopolysaccharide (LPS) (4, 5). TLR2 coupled with TLRs 1 and 6 recognises diacyl- and triacyl-lipopetides respectively (6). TLR3 recognises dsRNA (7), TLR5 recognises bacterial flagellin (8) while TLR9 recognises unmethylated CpG motifs (9). Once a TLR has recognised a PAMP it must recruit a TIR domain-containing adaptor to activate the subsequent signalling pathway. The first of these adaptors to be identified was MyD88. It plays a key role in TLR and IL-1R signalling (10, 11, 12) and the resulting signalling cascade has been extensively studied (reviewed in 13). Evidence suggests that it is involved in signalling from all TLRs with the exception of TLR3. MyD88-deficient mice failed to respond to IL-1 stimulation, or stimulation of TLR2, TLR5 and TLR9 (11). In the case of TLR4, activation of NF-κB and MAPK still occurred albeit in a delayed manner. In addition, the induction of dendritic cell maturation and the activation of the transcription factor IRF3 were unaffected in MyD88-deficient mice. This suggested that TLR4 requires more than just MyD88 to fully activate its response and that this response could be divided into two categories, the MyD88-dependent response and the MyD88-independent response. NF-κB and TNF production were not impaired in response to TLR3 suggesting that MyD88 is not involved in TLR3 signalling.

The next adaptor to be identified was Mal (MyD88 adaptor-like), which has also been called TIRAP (TIR domain-containing adaptor protein) (14, 15). It was originally thought that this could be the adaptor that mediated the MyD88-independent response to TLR4 but Mal-deficient mice proved that this was not the case and that Mal and MyD88 work together to activate the MyD88-dependent pathway. Like MyD88-deficient mice, Mal-deficient mice showed a delayed activation of NF-κB and MAPK in response to LPS while the activation of dendritic cell maturation and the transcription factor IRF3 were unaffected (15, 16). Mal-deficient mice respond normally to ligands for TLR5, TLR7, TLR9, IL-1 and IL-18 confirming the belief that MyD88 is the only adaptor required by these receptors. TLR3 signalling is also normal in Mal-deficient mice suggesting that neither Mal nor MyD88 are involved in this pathway. Interestingly, the signalling pathway activated by TLR2 was completely abolished in Mal-deficient mice suggesting that Mal and MyD88 are both required for the activation of this pathway (16).

Trif (TIR domain-containing adaptor inducing interferon-β) was the third adaptor to be discovered (17, 18). It was also called TIR-containing adaptor molecule-1 (TICAM-1). Trif, when over-expressed, activated NF-κB albeit to a much lesser extent than Mal or MyD88 but it was a much stronger activator of IFN-β (17). This suggested that it may be involved in the MyD88-independent pathway and Trif-deficient mice proved this (19). NF-κB activation in response to LPS was almost normal in these mice but when these cells were deficient of Trif and MyD88, the NF-κB response to LPS was totally abolished. In Trif-deficient mice the activation of IRF3 in response to LPS was totally abolished again suggesting that Trif is involved in the MyD88-independent pathway activated by TLR4. The activation of IRF3 by TLR3 was also abolished in Trif-deficient cells and the activation of NF-κB was severely impaired suggesting that Trif is the sole adaptor used by TLR3.

It was discovered that Trif could not bind directly to TLR4 (18) suggesting that a bridging adaptor is needed to bind it to TLR4. That bridging adaptor has now been discovered by several groups and is called TRAM (Trif-related adaptor molecule) (20) or TICAM-2 (TIR-containing adaptor molecule-2) (21) or TIRP (TIR domain-containing protein) (22).

TRAM binds directly to TLR4 but not to the other TLRs (21). Overexpression of TRAM led to a mild induction of IRF3, IRF7 and NF-κB, independent of MyD88. A dominant negative form of TRAM inhibited activation of NF-κB and IRF3 by LPS, but had no effect on the activation of either of these transcription factors by the TLR3 ligand, Poly(I:C). Overexpression of TRAM, along with Trif, lead to the translocation of IRF3 to the nucleus (20). A dominant negative form of Trif largely suppressed the ability of TRAM to activate NF-κB and IFN-β while MyD88 and Mal dominant negative mutants had no effect.

TRAM cannot function in Trif-knockdown RAW cells, suggesting that TRAM is working upstream of Trif on the TLR4 pathway. The generation of TRAM-deficient mice (23) added weight to this theory. These mice showed that TRAM was essential for activation of the MyD88-independent pathway in response to TLR4 and that it was not involved in other TLR pathways.

The inventors have now surprisingly found that the adapter molecule TRAM is rapidly phosphorylated by protein kinase C epsilon following the binding of LPS to the TLR4 receptor (Toll Like Receptor 4). It is defined that TRAM is phosphorylated by protein kinase C epsilon at the site of the serine 16 residue. Assays directed to monitoring the phosphorylation of TRAM may be a useful tool in determining the activation of TLR4 and in particular whether LPS signalling through the TLR4 receptor is functioning properly in different environments.

SUMMARY OF THE INVENTION

According to a first aspect of the present invention there is provided a method for determining the activation status of TRAM (Trif-related adaptor molecule), said method comprising the steps of:
  providing a cellular sample comprising TRAM, and
  monitoring TRAM for phosphorylation,
wherein the absence of phosphorylation of TRAM indicates that TRAM is not active.

As herein defined, the term 'activation status' means whether TRAM is involved in a cellular signalling pathway. Accordingly, activated TRAM, results from phosphorylation of TRAM at the serine 16 residue, with TRAM, in an active form, contributing to signalling mediated through the TLR4 receptor.

In a preferred embodiment of the assay, TRAM is contacted with a kinase under conditions permissive of phosphorylation. In one embodiment the kinase may be protein kinase C epsilon.

In a further embodiment of the assay, TRAM phosphorylation is monitored with regard to a control in order to determine phosphorylation.

In a further embodiment, TRAM phosphorylation is measured with regard to the presence of TRAM within the membrane of a cell. Phosphorylation of TRAM causes movement of TRAM out of the cell membrane.

Accordingly a further embodiment of this aspect of the invention provides for determining the phosphorylated state of TRAM by determining the presence or level of TRAM present in the cell membrane, wherein the absence or a decrease of the presence of TRAM within the membrane is indicative of TRAM being in a phosphorylated state wherein it moves out of the membrane.

Accordingly in one embodiment the method used to determine the phosphorylation of TRAM comprises a membrane depletion assay which determines and/or quantifies the presence and/or level of TRAM within a cell membrane.

Without being bound by theory, the inventors predict that the movement of TRAM out of the cell membrane following phosphorylation is caused by phosphorylation of the TRAM at the serine 16 residue causing a negative charge to be imparted which causes a repulsive force which results in movement of TRAM out of the membrane.

As herein described, the molecule referred to as TRAM (Trif-related adaptor molecule) may also be referred to as TICAM-2 (TIR-containing adaptor molecule-2) (21) or TIRP (TIR domain-containing protein) (22).

The above assays for determining the state of phosphorylation of TRAM can be further modified to allow the identification of candidate agents which can modulate TRAM activation.

Accordingly a further embodiment of this aspect of the invention provides a method for identification of modulator(s) of TRAM activity, said method comprising the steps of:
  (i) providing first and second cellular samples containing TRAM,
  (ii) contacting said first sample with a candidate modulator of TRAM,
  (iii) contacting said first and second samples with a kinase under conditions permissive of phosphorylation, and
  (iv) monitoring the phosphorylation status of TRAM, and comparing the phosphorylation of TRAM between said first and second samples,
wherein a difference in TRAM phosphorylation between said first and second samples identifies the candidate modulator as a modulator of TRAM activity.

In one embodiment, the kinase which phosphorylates TRAM is protein kinase C epsilon.

The modulator(s) identified according to the above assays of this aspect of the present invention may be a peptide or non-peptide molecule such as a chemical entity or pharmaceutical substance. Where the modulator is a peptide it may be an antibody, an antibody fragment, or a similar molecule with binding activity. Further, where the modulator is an antibody, preferably it is a monoclonal antibody.

A further aspect of the present invention provides for the use of a modulator identified according to the previous aspect of the invention in the preparation of a medicament of modulating the signalling mediated through the TLR4 receptor. In one embodiment signalling through the TLR4 receptor is upregulated. In a further, preferred embodiment, signalling mediated through the TLR4 receptor is downregulated.

A yet further aspect of the invention provides a kit for the determination of the phosphorylation of TRAM, the kit comprising a reference sample, means for determining the phosphorylation of TRAM and instructions for the performance of any of the assays of the invention using the methods of the first aspect of the invention.

In as much as the above aspects of the invention describes assay methods for assessing the phosphorylated state of TRAM and the identification of compositions useful for modulating the same, the present invention has further utility in the provision of an assay for assessing the activation of the TLR4 receptor by a ligand and in particular by LPS. Such an assay may be of significant value in the identification and development of compounds which may selectively up-regulate or down-regulate signalling through the TLR4 receptor. Such compounds would have significant utility as modulators of the signalling pathway which results from TLR4 binding and most specifically TLR4 binding by LPS (lipopolysaccharide).

According to a fourth aspect of the present invention there is provided an assay method for the detection of TLR4 activation by a ligand, the assay comprising the steps of:
  providing a cellular sample comprising cells expressing TLR4,
  bringing said cells into contact with the ligand, and
  detecting the phosphorylation of TRAM,
wherein phosphorylation of TRAM is indicative of the binding of a ligand to TLR4.

Preferably the level of phosphorylation can be compared to a control sample, such as the same type of cells which are not exposed to the ligand. Alternatively, the test sample can be controlled to a known, pre-determined reference value.

By determining phosphorylation it is possible to identify candidate agents which modify the phosphorylation of TRAM through their interaction with the TLR4 receptor.

A further aspect of the present invention provides for the use of a ligand identified according to the previous aspect of the invention in the preparation of a medicament of modulating the signalling mediated through the TLR4 receptor. In one embodiment signalling through the TLR4 receptor is upregulated.

Accordingly a further embodiment of the fourth aspect of the present invention provides an assay for identifying an agonist of the TLR4 receptor, said assay comprising the steps of:
providing a cellular sample including cells which express TLR4,
exposing the cells to a test compound,
detecting the phosphorylation of TRAM,
wherein an increase in the phosphorylation of TRAM is indicative of activation of the TLR4 receptor following binding of the test compound thereto.

In one embodiment the agonist of the TLR4 receptor induces or upregulates signalling mediated by the TLR4 receptor.

A further aspect of the present invention provides for the use of a compound identified according to the previous aspect of the invention in the preparation of a medicament of modulating the signalling mediated through the TLR4 receptor. In one embodiment signalling through the TLR4 receptor is upregulated.

A further alternative embodiment of this aspect of the present invention provides an assay for identifying an antagonist of the TLR4 receptor, said assay comprising the steps of:
providing a cellar sample including cells which express TLR4,
exposing the cells to a test compound,
detecting the phosphorylation of TRAM,
wherein a decrease in the phosphorylation of TRAM in the presence of a test compound, when compared to the absence of a test compound is indicative of the test compound being an antagonist.

In one embodiment the antagonist of the TLR4 receptor prevents or downregulates signalling mediated by the TLR4 receptor.

In one embodiment, the assay further includes the step of exposing the cells to an agonist prior to exposure to the test compound.

A further aspect of the present invention provides for the use of a compound identified according to the previous aspect of the invention in the preparation of a medicament of modulating the signalling mediated through the TLR4 receptor. In one embodiment signalling through the TLR4 receptor is upregulated.

A yet further aspect of the invention provides a kit for the performance of an assay for the determination of the activation of TLR4, the kit including a sample, and instructions for performance of the assays in accordance with the fourth aspect of the invention.

The inventors have, through substantial experimentation, identified that protein kinase C epsilon (PKCε) is the kinase which phosphorylates TRAM. Inhibition of phosphorylation by protein kinase C epsilon impairs the ability of TRAM to activate NK-κB and IFN-β.

Accordingly a sixth aspect of the present invention provides an assay method for determining compounds which act as inhibitors of the function of protein kinase C epsilon, the methods comprising the steps of:
providing a candidate compound,
bringing the candidate compound into contact with protein kinase C epsilon,
determining the presence or absence of the ability of protein kinase C epsilon to phosphorylate TRAM,
wherein the absence of phosphorylation of TRAM is indicative of the blocking of the function of protein kinase C epsilon by the candidate compound.

Directly inhibiting the protein kinase C epsilon molecule will not only prevent phosphorylation of TRAM but also inhibit the other cellular functions of protein kinase C epsilon. However the inventors have identified the specific domain of TRAM to which protein kinase C epsilon binds and this opens up the possibility of selective inhibition of phosphorylation of TRAM without causing the inhibition of other cellular functions of protein kinase C epsilon.

Accordingly, an alternative embodiment of this aspect of the invention provides an assay for the identification of compounds which prevent the phosphorylation of TRAM by protein kinase C epsilon, said assay comprising the steps of:
providing a candidate compound,
bringing the candidate compound into contact with TRAM,
exposing TRAM to protein kinase C epsilon in conditions suitable for phosphorylation to occur, and
determining the presence or absence of phosphorylation of TRAM,
wherein the absence of phosphorylation is indicative of the blocking of the interaction between protein kinase C epsilon and TRAM.

In a preferred embodiment the compound selectively inhibits phosphorylation of TRAM by protein kinase C epsilon.

In one embodiment the method includes the step of determining the ability of a compound to bind TRAM at or in the region of the domain corresponding to the serine 16 residue present on TRAM in order to prevent the phosphorylation of that serine residue by protein kinase C epsilon.

In various further aspects, the present invention relates to screening and assay methods and to substances identified thereby.

Novel compounds identified using the assays of the invention form a further independent aspect of the invention. Such compounds or modulators may be provided in pharmaceutical compositions.

A modulator, or compound which modulates as identified according to the assays of the present invention may be a peptide or non-peptide molecule such as a chemical entity or pharmaceutical substance. Where the modulator is a peptide it may be an antibody, an antibody fragment, or a similar binding fragment. Further, where the modulator is an antibody, preferably it is a monoclonal antibody.

A monoclonal antibody, antibody fragment or similar binding molecule with specificity for TRAM, which in particular binds to, or causes full or partial blocking of the serine-16 residue at the region to which protein kinase C epsilon binds in order to facilitate phosphorylate of TRAM has utility in the inhibition of the phosphorylation of TRAM and accordingly may prevent it facilitating downstream signalling activities following the binding of LPS to the TLR4 receptor.

Accordingly a further aspect of the invention provides a specific binding member which comprises an antigen binding domain, wherein the antigen binding domain has specificity to the serine-16 residue of TRAM.

In one embodiment the present invention provides an immunoglobulin which specifically binds or blocks binding to the serine-16 residue of TRAM.

A yet further embodiment provides an immunoglobulin which prevents the phosphorylation of the serine-16 residue of TRAM by protein kinase C epsilon.

Also encompassed within the scope of this aspect of the invention are specific binding members which bind to TRAM in order to prevent phosphorylation by protein kinase C epsilon.

Endotoxins are composed of a lipopolysaccharide (LPS) complex which includes Lipid A and polysaccharide. LPS binds to the TLR4 receptor, this resulting in a downstream signalling cascade which induces an appropriate immune response.

LPS-mediated or endotoxin-mediated conditions such as sepsis and septic shock can frequently result in mortality. Accordingly, a method of down-regulating or inhibiting the TLR4 mediated immune response pathway would be desirable as a treatment method for LPS mediated conditions such as sepsis.

The present invention, through the observation that TRAM is phosphorylated by protein kinase C epsilon following LPS binding to TLR4 provides a potential route by which the interaction between LPS and intracellular kinases can be regulated. This may accordingly provide a powerful mechanism to disrupt LPS signalling.

Accordingly the present invention may be used in the treatment of LPS-mediated conditions.

The assay of the present invention and compounds of biological significance to the TLR4 signalling pathway which are realised by means of the use of said assay may have specific utility in the treatment in a number of medical conditions, most specifically endotoxin and LPS mediated conditions, for example sepsis.

Accordingly, a seventh aspect of the present invention provides an assay for identifying compounds suitable for use in the treatment of endotoxin mediated conditions, said assay comprising the steps of:
  providing a candidate compound,
  bringing the candidate compound into contact with TRAM,
  determining the presence or absence of phosphorylation of TRAM by the candidate compound,
wherein modulation of TRAM phosphorylation is indicative of the utility of that compound.

In one embodiment the endotoxin mediated condition is sepsis or septic shock.

A yet further aspect of the invention provides a method of treating LPS mediated conditions, said method comprising the step of inhibiting the phosphorylation of TRAM.

In one preferred embodiment of this aspect of this invention, the inhibition of phosphorylation of TRAM is provided by blocking the binding of protein kinase C epsilon to TRAM.

In one embodiment, blocking of the binding of protein kinase C epsilon to TRAM is facilitated by means of a compound which inhibits binding of protein kinase C epsilon to the serine 16 region where it effects phosphorylation.

In a yet further embodiment, the compound binds directly to the serine-16 site at which protein kinase C epsilon effects phosphorylation of TRAM. Alternatively, the inhibitor binds to a site on TRAM which prevents protein kinase C epsilon accessing the binding site on TRAM required to facilitate phosphorylation of the serine-16 residue.

The sequence of TRAM, is defined as SEQ ID NO:1 is: MGIGKSKINSCPLSLSWG (SEQ ID NO: 1). Serine 16 is the last serine in the sequence.

Alternatively, a molecule is provided which competes with protein kinase C epsilon for binding to TRAM at a location suitable to phosphorylate the serine-16 residue.

A further still aspect of the present invention provides a method of treating an LPS mediated condition such as sepsis in a subject comprising administering to said subject a therapeutically effective amount of a molecule which inhibits phosphorylation of TRAM.

In one preferred embodiment of this aspect of the invention, the molecule prevents phosphorylation of TRAM by protein kinase C epsilon.

The endotoxin mediated condition may, in particular, be caused by LPS which can result in fever, changes in white blood cell count, disseminated intravascular coagulation, hypotension, shock and death.

In one preferred embodiment, the endotoxin mediated condition is sepsis.

A further aspect of the present invention provides for the use of an inhibitor of protein kinase C epsilon in the preparation of a medicament for the treatment of an endotoxin mediated condition.

Accordingly a further aspect of the invention provides a specific binding member which comprises an antigen binding domain, wherein the antigen binding domain has specificity to protein kinase C epsilon.

In one embodiment the present invention provides an immunoglobulin which specifically binds or blocks binding to protein kinase C epsilon.

A yet further aspect of the present invention provides for the use of an inhibitor of protein kinase C epsilon in the preparation of a medicament for the treatment of sepsis.

A further still aspect of the present invention provides for the use of a compound which prevents the phosphorylation of TRAM in the preparation of a medicament for the treatment of an endotoxin mediated disease such as sepsis.

A further still aspect of the invention provides a method of treating a medical condition using a compound identified by any one of the assay methods according to any one of the foregoing aspects of the present invention.

Signalling mediated through the TLR4 receptor may also be involved with other immune responses aside those mediated by endotoxins. For example, signalling through the TLR4 receptor may be involved in inflammatory diseases, hence modulation of the ligand binding capacity of, and signal transduction by, and downstream of the TLR4 receptor may effect inflammatory diseases such as arthritis and atherosclerosis. In some autoimmune conditions, a candidate ligand or modulator of the TLR4 receptor has yet to be identified. However, in such instances, it would be suggested that endogenous factors made by inflamed or damaged tissue would act on the TLR4 receptor or its associated signalling pathway.

Accordingly, a yet further aspect of the present invention provides an assay for identifying compounds suitable for use in the treatment or prophylaxis of an inflammatory or immune-mediated disorder, said assay comprising the steps of:
  providing a candidate compound,
  bringing the candidate compound into contact with TRAM,
  determining the presence or absence of phosphorylation of TRAM by the candidate compound,
wherein modulation of TRAM phosphorylation is indicative of the utility of that compound.

In preferred embodiments, the immune mediated disorder may be arthritis or atherosclerosis.

A yet further aspect of the present invention provides for the use of an inhibitor of protein kinase C epsilon in the preparation of a medicament for the treatment or prophylaxis of an inflammatory condition or an immune-mediated disorder.

A further still aspect of the present invention provides for the use of a compound which prevents the phosphorylation of TRAM in the preparation of a medicament for the treatment or prophylaxis of an inflammatory or immune-mediated disorder.

In a still further aspect of the present invention, there is provided a method of treating a condition associated with signalling through the TLR4 receptor following binding thereto by LPS, in a patient in need of treatment thereof, said method comprising administration of a compound identified in accordance with any one of the assays of the present invention.

Preferred features of each aspect of the invention are as for each of the other aspects mutatis mutandis unless the context demands otherwise.

Assays

The invention provides assay systems and screening methods for determining TRAM phosphorylation and further for monitoring TLR4 activation by means of the occurrence of TRAM phosphorylation. As used herein, an "assay system" encompasses all the components required for performing and analysing results of an assay that detects and/or measures a particular event or events.

A variety of assays are available to detect the phosphorylation status of a target molecule or protein.

In one embodiment, the assay will use a phosphor-specific antibody which is directed to the region of TRAM which undergoes phosphorylation. Most preferably, this antibody will bind to TRAM in the region of or proximal to the serine 16 residue.

The amino acid sequence of TRAM, is defined as SEQ ID NO:1 which is as follows: MGIGKSKINSCPLSLSWG (SEQ ID NO: 1).

In a preferred embodiment, the assays of the invention will employ the technique known as Western Blotting. An antibody will be used in a Western Blot of samples from cells stimulated with a ligand to the TLR receptors, such as LPS, using standard methodology which will be well known to the man skilled in the art.

In a further embodiment, the antibody can be used in other assay formats. For example, assays based on peptide fragments from TRAM could be used in in-vitro kinase assays instead of the whole protein.

It is preferred, though not essential that the screening assays employed in the present invention are high throughput or ultra high throughput and thus provide an automated, cost-effective means of screening.

DETAILED DESCRIPTION OF THE INVENTION

Treatment

The term 'treatment' as used herein refers to any regime that can benefit a human or non-human animal. The treatment may be in respect of an existing condition or may be prophylactic (preventative treatment). Treatment may include curative, alleviation or prophylactic effects.

Pharmaceutical Compositions

The present invention further extends to pharmaceuticals and to pharmaceutical compositions for the modulation of the phosphorylation of TRAM through an alteration of its phosphorylation state or through preventing its phosphorylation.

Accordingly, a further aspect of the present invention provides a pharmaceutical composition for use in the modification of an immune response wherein the composition includes, as an active ingredient, a compound which modifies the phosphorylation of TRAM through promoting or blocking phosphorylation.

Pharmaceutical compositions according to the present invention, and for use in accordance with the present invention may comprise, in addition to active ingredient, a pharmaceutically acceptable excipient, carrier, buffer stabiliser or other materials well known to those skilled in the art.

Such materials should be non-toxic and should not interfere with the efficacy of the active ingredient. The precise nature of the carrier or other material will depend on the route of administration.

Dose

The composition is preferably administered to an individual in a "therapeutically effective amount", this being sufficient to show benefit to the individual. The actual amount administered, and rate and time-course of administration, will depend on the individual and condition being treated.

The optimal dose can be determined based on a number of parameters including, for example the age of the individual, the magnitude of the immune response to be inhibited or induced, the precise form of the composition being administered and the route of administration.

The composition may be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7$^{th}$ Edition ISBN 0-683305-72-7 the entire disclosures of which is herein incorporated by reference.

Antibodies

In the context of the present invention, an "antibody" should be understood to refer to an immunoglobulin or part thereof or any polypeptide comprising a binding domain which is, or is homologous to, an antibody binding domain.

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced.

The antibody may be an intact antibody or a fragment thereof. Fragments of a whole antibody can perform the function of antigen binding. Examples of such binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site; (viii) bispecific single chain Fv dimers and (ix) multivalent or multispecific fragments constructed by gene fusion.

Antibodies can be modified in a number of ways and accordingly the term "antibody" should be construed as covering any binding member or substance having a binding domain with the required specificity.

The antibody of the invention may be a monoclonal antibody, or a fragment, derivative, functional equivalent or homologue thereof. The constant region of the antibody may be of any suitable immunoglobulin subtype.

The term "antibody" includes antibodies which have been "humanised" or produced using techniques such as CDR grafting. Such techniques are well known to the person skilled in the art.

Production of Antibodies

Specific binding members of and for use in the present invention may be produced in any suitable way, either naturally or synthetically. Such methods may include, for example, traditional hybridoma techniques, recombinant DNA techniques, or phage display techniques using antibody libraries. Such production techniques would be known to the person skilled in the art, however, other antibody production techniques are described in Antibodies: A Laboratory Manual, eds. Harlow et al., Cold Spring Harbor Laboratory, 1988.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

The present invention will now be described with reference to the following examples which are provided for the purpose of illustration and are not intended to be construed as being limiting on the present invention, and further, with reference to the figures.

BRIEF DESCRIPTION OF THE DRAWINGS

FIG. 1: TRAM was cloned from cDNA using (a) primers TRAM-N (SEQ ID NO:2) and TRAM-C (SEQ ID NO:3), targeting the 5' and 3' ends of TRAM, respectively, and (b) the rsulting PCR product was cloned into several vectors, (c) Site directed mutagenesis was performed using specific primers 4Ser (SEQ ID NO:4) and 4SerRev (SEQ ID NO:5) to mutate The first 4 serines in TRAM to alanines and specific primers Ser 16 (SEQ ID NO:6) and Ser16rev (SEQ ID NO:7) to mutate the serine at position 16 alone to an alanine.

FIG. 2: (a) GST-TRAM is phosphorylated upon incubation with THP1 lysates that have been treated with LPS for varying lengths of time. (b) This phosphorylation of TRAM does not occur when the cells are treated with PolyI:C. (c) This LPS-dependent phosphorylation is abolished when the first 4 serines of TRAM are mutated to alanines. (d) Following GST-TRAM pulldowns with lysates from THP1 cells treated for 30 min with LPS, the samples were incubated with increasing amounts of the pan PKC inhibitor, Bisindolylmaleimide (Bis), for 1 hour. This caused a decrease in the phosphorylation of TRAM. (e) Immunodepletion of the THP1 lysates was performed using a PKCε antibody, a PKCζ antibody or an IgG control antibody prior to incubation with the GST-TRAM. Removal of PKCε from the lysates prevented LPS-dependent phosphorylation of TRAM. (f) Lysates taken from PKCε-deficient MEFs cannot phosphorylate GST-TRAM while MEFs reconstituted with PKCζ can. (g) Recombinant PKCε (rePKCε) or PKCζ (rePKCζ) was incubated directly with GST-TRAM for 15 minutes prior to a kinase assay being performed. rePKCε phosphorylated WT-TRAM but not Mal.

FIG. 3: (a) When the serine at position 16 is mutated to an alanine, GST-TRAM can no longer be phosphorylated following incubation with THP1 lysates. (b) pcDNA3.1 alone (eV), WT-TRAM/pcDNA3.1 and Ser16-TRAM/pcDNA3.1 were all transfected into HEK293 cells seeded in 96-well plates. The NF-κB or ISRE-luciferase reporter gene and the Renilla luciferase internal control plasmid were also transfected in. 24 hours later the reporter gene activity was measured and the data expressed as mean fold stimulation relative to control levels. The graph shows that WT-TRAM can activate both the NF-κB and ISRE pathways while the Ser16-TRAM mutant cannot activate either pathway. (c) a similar experiment was then carried out in HEK293-TLR4 cells and 24 hours post transfection the cells were incubated with and without LPS (1 μg/ml) for 6 hours. The results show that WT-TRAM increases the ability of LPS to activate both NF-κB and ISRE while the Ser16-TRAM mutant acts as a dominant negative and reduces the ability of LPS to stimulate NF-KB and ISRE. (d) HEK293 cells were incubated with and without the PKC inhibitor, Bisindolylmaleimide (Bis), for 1 hour prior to transfection with pcDNA3.1, MyD88/pcDNA3.1 or WT-TRAM/pcDNA3.1 and the NF-κB-luciferase reporter gene and Renilla luciferase internal control plasmid. The inhibitor had no effect on the ability of MyD88 to activate the NF-κB pathway but it inhibited the ability of TRAM to activate this pathway.

FIG. 4 shows that TRAM is phosphorylated on the Serine 16 residue. (a) HEK293-TLR4 cells overexpressing FLAG-tagged TRAM were stimulated with 1 μg/ml LPS for 30 min. FLAG-tagged TRAM was immunoprecipitated using an antibody to FLAG and blotted with a phosphoserine antibody. (b) THP1 cells incubated with and without the PKC inhibitor BIS for 1 hour prior to stimulation with LPS, (c) PKCε$^{-/-}$ MEFs and PKCε$^{-/-}$ MEFs that had been reconstituted with PKCε following stimulation with 1 μg/ml LPS for the indicated lengths of time and (d) PKCε$^{-/-}$ MEFs and PKCε$^{-/-}$ MEFs that had been reconstituted with PKCε following stimulation with LPS, polyI:C or MALP2 for 30 minutes.

FIG. 6: TRAMS16A is attenuated relative to WT TRAM in reconstituting TRAM-deficient MEFs. WT TRAM, TRAMS16A and empty vector were transfected into TRAM-deficient MEFs. 24 hours post transfection. (a) Cells were stimulated with LPS (1 μg/ml) for a further 24 h and the culture supernatants were assayed for RANTES by ELISA.

(b) Cells were stimulated with LPS (1 µg/ml) for 30 minutes and the lysates were assayed for p38 by western blot. Results shown are representative of at least three experiments.

Figure 7:
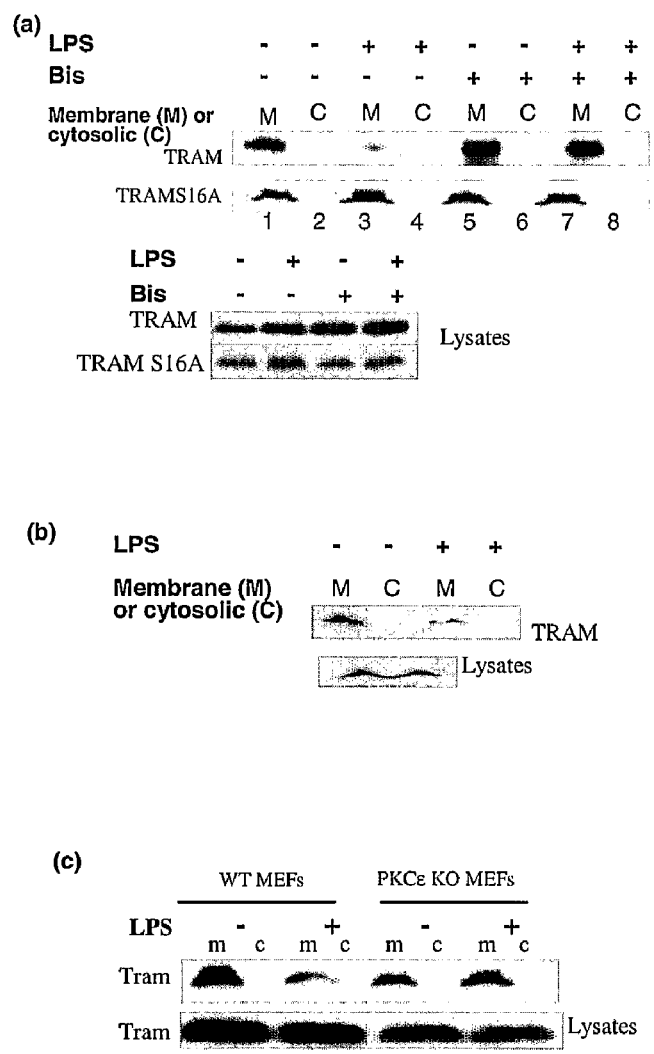

FIG. 7 shows that the amount of TRAM present in the membrane fraction was decreased upon LPS stimulation suggesting that TRAM is disappearing from the membrane.

FIG. 8 shows when the serine 16 residue was mutated to a glutamic acid, this mutation caused a significant decrease in the amount of TRAM present in the membrane (FIG. 8a, compare lane 3 to 1) suggesting that the phosphorylation of TRAM on Serine 16 causes depletion of TRAM from the membrane, and further that depletion of endogenous TRAM in THP1 cells treated with LPS (FIG. 8b) was also detected, and further that PKCε−/− MEFs FLAG-TRAM did not become depleted from the membrane upon LPS stimulation (FIG. 8c). This evidence suggests that the phosphorylation of TRAM on Serine 16 by PKCε is required for TRAM to be depleted from the membrane.

EXAMPLES

Materials and Methods

Cells: HEK293 cells and HEK293 cells stably transfected with TLR4 (HEK293-TLR4) were cultured in Dulbecco's Modified Eagles medium (DMEM) supplemented with 10% Fetal calf serum (FCS), 100 Units/ml penicillin, 100 mg/ml streptomycin and 2 mM Glutamine. THP1 cells were cultured in RPMI supplemented with 10% FCS, 100 Units/ml penicillin, 100 mg/ml streptomycin and 2 mM Glutamine.

Reverse Transcriptase-Polymerase Chain Reaction (RT-PCR): cDNA was generated using spleen mRNA (BD Biosciences) as a template. 1-5 µg RNA was incubated with 0.1 µg random primers and brought to a final volume of 5 µl with DEPC-treated water.

This was incubated at 70° C. for 10 min and then 4° C. for 2 min. Reverse transcription was carried out using the moloney murine leukemia virus reverse transcriptase (MMLV-RT) enzyme. 4 µl 5× buffer (250 mM TrisCl pH 8.3, 375 mM KCl and 15 mM $MgCl_2$) was added along with 2 µl 100 mM DTT, 1 µl RNasin (40 unit/ml), 1 µl 10 mM dNTP, 1 µl MMLV-RT (200 unit/µl) and 6 µl DEPC-treated water. This reaction was incubated at 37° C. for 1 hour and then 95° C. for 2 min to inactivate the enzyme. 5 µl of this reaction was used as a template for a PCR reaction using specific primers to the 5' and 3' ends of TRAM. 1×DNA polymerase buffer (1 mM TrisCl pH 9.0, 5 mM KCl and 0.01% Triton® X-100), 0.2 mM of each dNTP, 2.5 u Taq DNA polymerase, 0.5 µM of each specific oligonucleotide primer and 0.5-3 mM $MgCl_2$ were added to the template DNA and the reaction mix was made up to a final volume of 50 µl using PCR grade water. 30 cycles of 94° C. for 1 min, 55° C. for 1 min and 72° C. for 2 min were performed in a thermal cycler. The PCR products were analysed by agarose gel electrophoresis.

Cloning of TRAM into a GST expression vector and a mammalian expression vector: The TRAM PCR product was ligated into the pGEX-KG vector (Pharmacia) and into the pcDNA3.1 vector (Invitrogen). Firstly, the PCR product and vector were digested in separate reactions. 5-10 unit restriction endonuclease (NEB), 1× restriction enzyme buffer, ±1×BSA and 1-10 µg DNA were made up to 10 µl with sterile water and incubated at 37° C. for 2 hours. The digested products were then purified using a PCR purification kit (Qiagen). A ligation reaction consisting of 1 unit T4 DNA ligase (1 unit/µl) (Promega), 2 µl T4 10× reaction buffer, 100-150 ng digested vector DNA and 200-400 ng digested PCR product, was made up to 20 µl with sterile water. This ligation mixture was left overnight at 4° C. and then transformed into BL21(DE3) cells (Stratagene).

Site directed mutagenesis of TRAM: The Quickchange® site directed mutagenesis kit (Stratagene) was used to mutate certain bases in the TRAM gene. The manufacturer's instructions were followed using primers containing the desired mutation.

Expression and purification of GST-TRAM: The BL21 (DE3) containing the TRAM-pGEX vector were grown overnight at 37° C. in 10 ml LB broth in a shaking incubator. The next day the 10 ml was placed in 500 ml LB broth and grown to an OD of 0.6-0.8. IPTG was added to the culture to a final concentration of 0.2 mM and this culture was incubated at 30° C. for a further 4 hours. The culture was then spun down in a GSA rotor in a Sorvall RC5C centrifuge at 8,000 rpm for 15 min. The pellet was resuspended in 25 ml of NETN buffer (20 mM Tris-Cl, 100 mM NaCl, 1 mM EDTA, 0.5% NP40, 10 µg/ml leupeptin, 10 µg/ml pepstatin, 1 mM PMSF, pH 8.0), sonicated for 5 min using a sonicator (Branson Sonifer 250) and centrifuged at 18,000 rpm for 45 min. The supernatant was added to 600 l Glutathione sepharose beads (Amersham) and incubated at 4° C. for 2 hours. The beads were then washed 5 times in 15 ml NETN buffer and resuspended in 600 µl NETN buffer.

Luciferase reporter gene assays: HEK293 or HEK293-TLR4 cells were seeded in 96 well plates at a density of $1 \times 10^5$ cells/ml. The following day the cells were transfected with the luciferase reporter plasmid of choice and the expression vectors of choice using Genejuice (Novagen), following the manufacturer's instructions. For experiments involving the detection of NF-κB and IRF3 activation, 80 ng of the NF-κB or IRSE-luciferase reporter gene (Stratagene) were transfected into the cells along with 40 ng of the Renilla luciferase internal control plasmid (Stratagene). After 24 hours the cells were lysed in passive lysis buffer (Promega) and reporter gene activity was measured using a luminometer. The data was expressed as mean fold stimulation relative to control levels.

Kinase assay: THP1 cells were seeded at $2 \times 10^5$ cells/ml in a T175 flask (Sarstedt) and incubated overnight at 37° C. The following day 30 ml of cells were treated with and without LPS in 50 ml falcon tubes (Sarstedt) for 1 hour. The cells were collected by centrifugation, washed once in PBS and lysed in 1 ml buffer (10% glycerol (v/v), 50 mM NaF, 20 mM Tris-Cl pH 8.0, 2 mM EDTA, 137 mM NaCl, 1% NP-40, 1 mM PMSF, 10 µg/ml leupeptin, 1 mM $Na_3VO_4$) for 10 minutes. The cell debris was centrifuged for 10 min at 13,000 rpm and the supernatant was removed to a fresh tube for use in the kinase assay. 50 µl of the purified GST-TRAM on the Glutathione beads was placed in an eppendorf tube and the appropriate lysate was added to the tube and incubated for 2 hours at 4° C. The beads were spun down at 2,000 rpm for 5 min and then washed three times in kinase buffer (20 mM HEPES, pH 7.5, 10 mM MgAc, 0.03% Trition, 100 µg/ml phosphotidylserine, 20 mM β-glycerol phosphate, 0.01% (w/v) leupeptin and 100 µM $Na_3VO_4$). These beads were then resuspended in 30 µl kinase buffer containing 20 µM cold ATP and 5 µCi [$\gamma^{32}P$] ATP and incubated at 37° C. for 30 min. 20 µl sample buffer (50 mM Tris-Cl, pH 6.8, 10% glycerol (v/v), 2% SDS (w/v), 0.1% bromophenol blue (w/v) and 5% β-mercaptoethanol) was added to the tube and the sample was boiled for 5 mins. The sample was then run on a 10% SDS-PAGE gel and transferred to nitrocellulose. The nitrocellulose was placed in a autorad cassette (Kodak) and an piece of X-ray film was placed on top. This was left at −80° C. overnight and the film was then developed.

Membrane fractionation: HEK293-TLR4 cells were seeded at $1\times10^5$ cells/ml overnight and then transfected with the appropriate plasmids. 24 hrs post-transfection the cells were treated as directed in the results section and then scrapped into 300 µl of membrane buffer (20 mM Tris, pH 7.5, 10 mM $MgCl_2$, 1 mM EDTA, 250 µM sucrose, 200 µM PMSF). The cells were lysed using 30 strokes of a dounce homogenizer and spun in hardwall Beckman tubes at 100,000 rpm for 1 hr at 4° C. The supernatant, i.e. the cytosolic fraction, was removed to a fresh tube and the pellet, i.e. the membrane fraction, was resuspended in 50 µl sample buffer (50 mM Tris-Cl, pH 6.8, 10% glycerol (v/v), 2% SDS (w/v), 0.1% bromophenol blue (w/v) and 5% β-mercaptoethanol). The cytosolic fraction was concentrated down to 50 µl using a centricon YM-10 (Millipore). The samples were run on a 12% SDS-PAGE gel.

Production of a Phospho-Specific TRAM Antibody

Fabgennix (Texas, USA), using a synthetic peptide corresponding to amino acids 7 to 21 of TRAM (KIN SCP LSL SWG KRH) with a phosphoserine incorporated instead of the serine at amino acid 16, generated and purified a phospho-specific antibody towards TRAM phosphorylated on Serine 16. The validity of the antibody was confirmed when the band predicted to the phosphorylated TRAM was not present in samples taken from TRAM-deficient MEFs (data not shown).

RANTES ELISA

The indicated cells were seeded at $1\times10^5$ cells/ml overnight in 24 well plates and then transfected with the appropriate plasmids. 24 hours post-transfection the cells were treated with the appropriate stimuli for 24 hours. Using a 1 in 5 dilution of the supernatant as the sample, a RANTES ELISA was performed, using the R&D systems' mouse RANTES kit, following the manufacturer's instructions.

IRF3 Dimerisation Assay

The appropriate cells were seeded at $2\times10^5$ cells/ml overnight and then treated with the appropriate stimuli. The cells were washed in PBS and scrapped into 100 µl non-reducing sample buffer (50 mM Tris-Cl, pH 6.8, 10% glycerol (v/v), 0.1% bromophenol blue (w/v) and 5% β-mercaptoethanol). 20 µl of this was run on a non-reducing PAGE gel, transferred onto nitrocellulose and blotted for IRF3.

Results

Cloning of the TRAM gene and generation of mutants: The cDNA sequence from TRAM was retrieved from Genebank (Accession number NM_021649). Specific primers to the 5' and 3' end of TRAM (FIG. 1a) were used to amplify up the TRAM cDNA using mRNA generated from the spleen (FIG. 1b). This cDNA was cloned into the pGEX-KG vector to allow for expression of a GST-TRAM fusion protein in bacteria. It was also cloned into the mammalian expression vector pcDNA3.1. To generate mutants of TRAM site directed mutagenesis was performed. Primers were designed (FIG. 1c) to allow for the mutation of the serines at position 6, 10, 14 and 16 (called 4Ser mutant). Primers were also designed to mutate Serine 16 alone (called Ser16 mutant).

TRAM is phosphorylated upon LPS stimulation: TRAM is myristoylated, and in resting cells is located in the membrane (unpublished data). Several myristoylated proteins undergo an electrostatic switch which involves them being phosphorylated and repelled from the membrane. An assay was therefore devised to determine if TRAM was phosphorylated. Purified GST-TRAM on glutathione beads was incubated for 2 hours with lysates from THP1 cells, that had been treated with and without LPS. The samples were then centrifuged causing GST-TRAM on the glutathione beads, along with any proteins it interacted with, to be pulled down. A kinase assay was then performed, by incubating the beads with $[\gamma^{32}P]$ ATP for 30 minutes. The samples were then run on a 10% SDS-PAGE gel, transferred onto nitrocellulose and the incorporated radioactivity was measured using X-ray film. The results (FIG. 2a) show that TRAM is indeed phosphorylated and that this phosphorylation is LPS dependent. This phosphorylation did not occur when the cells were treated with other stimuli, such as PolyI:C (FIG. 2b).

4 serines closest to the N terminus were identified. These 4 serines were subsequently mutated.

Following this mutation, LPS dependent phosphorylation was abolished (FIG. 2c).

Phosphorylation of TRAM

Protein Kinase C has been shown to phosphorylate the myristoylated protein, MARCKS, so to investigate if TRAM was phosphorylated by PKC, the pan PKC inhibitor bisindolylmaleimide (Bis) was used. As above, GST-TRAM was incubated with lysates from THP1 cells, treated with LPS and was pulled down using Glutathione beads. Increasing amounts of Bis were added to the beads for 1 hour and then the kinase assay was performed as above. Bis inhibited LPS dependent phosphorylation of TRAM (FIG. 2c). This strongly indicated that a member of the PKC kinase family was responsible for phosphorylation of TRAM in response to LPS.

Immunodepletion of the THP1 lysates was perform by incubating the lysates with a PKCε specific antibody (Santa Cruz) attached to protein G beads (Sigma). A PKC zeta (PKCζ) antibody was used as a control to check for specificity. The antibody was removed by centrifugation, removing PKCε or PKCζ from the lysates. A control IgG antibody was also used. These lysates were then incubated with GST-TRAM as above and a kinase assay was performed. FIG. 2e shows that the removal of PKCε from the lysates abolishes the phosphorylation of TRAM. This suggests that PKCε is phosphorylating TRAM in response to LPS. The removal of PKCζ had no effect on the phosphorylation of TRAM suggesting that PKCζ does not phosphorylate TRAM. This theory was further strengthened by the fact that recombinant PKCε (reP-KCε) (Calbiochem) phosphorylated GST-TRAM (FIG. 2g) and lysates from PKCε-deficient MEFs could not phosphorylate GST-TRAM (FIG. 2f). Recombinant PKCζ did not phosphorylate TRAM again suggesting specificity (FIG. 2g). Serine 16 is a candidate for PKCε phosphorylation so we mutated serine 16 to an alanine and found that the LPS dependent phosphorylation of TRAM was severally impaired (FIG. 3a).

As the serine at position 16 is the only one of four serines that is conserved in the mouse, this serine was mutated. LPS dependent phosphorylation of TRAM was severally impaired (FIG. 3a).

To investigate if this phosphorylation of TRAM was essential for it to function properly, the serine at position 16 was mutated to an alanine and the ability of this mutant to drive the NF-κB and IRF3 pathways was investigated. WT-TRAM or the Ser16-TRAM were transfected into HEK293 cells along with either the NF-κB or ISRE-luciferase reporter gene. As shown previously, TRAM can drive both NF-κB and ISRE luciferase. However, when the Serine 16 was mutated TRAM could no longer activate either pathway (FIG. 3b).

Mutating the Serine 16 also reduced the ability of LPS to stimulate the NF-κB and ISRE pathways (FIG. 3c). This mutant must act as a dominant negative on these pathways. Further evidence that phosphorylation of TRAM by PKC is essential for it to function correctly is the fact that the PKC inhibitor, Bisindolylmaleimide, inhibits the ability of TRAM to activate the NF-κB pathway but has no effect on MyD88

(FIG. 3d). This evidence suggests that Serine 16 needs to be phosphorylated by PKCε for TRAM to function properly.

In order to confirm that phosphorylation of the serine 16 residue was sufficient to allow TRAM to leave the membrane, the serine 16 residue was mutated to a glutamic acid. The resulting mutant (ser16Glu) served as a positive glycosylation control, wherein the glutamic acid residue mimics the serine residue when it is in a glycosylated state. This mutation caused a significant decrease in the amount of TRAM present in the membrane (FIG. 8a, compare lane 3 to 1) suggesting that the phosphorylation of TRAM on Serine 16 causes depletion of TRAM from the membrane.

Depletion of endogenous TRAM in THP1 cells treated with LPS (FIG. 8b) was also detected. Finally, in PKCε-/- MEFs FLAG-TRAM did not become depleted from the membrane upon LPS stimulation (FIG. 8c). This evidence suggests that the phosphorylation of TRAM on Serine 16 by PKCε is required for TRAM to be depleted from the membrane.

Endogenous TRAM is Phosphorylated on Serine 16

We tested phosphorylation of overexpressed TRAM using a phosphoserine antibody. HEK293-TLR4 cells transfected with FLAG-TRAM and stimulated with LPS. FLAG-TRAM was immunoprecipitated from the cells and lysates were blotted with an anti-phosphoserine antibody. As can be see from FIG. 4a, TRAM showed an increase in serine phosphorylation in cells treated with LPS for 30 minutes.

In order to establish whether endogenous TRAM is phosphorylated on serine 16 by PKCε, an antibody was raised to a synthetic peptide comprising of amino acid 7 to 21 of TRAM with a phosphoserine inserted instead of a serine at amino acid 16.

Immunoblotting lysates from THP1 cells treated with LPS, showed TRAM phosphorylation on serine 16 appearing after 15 minutes and peaking at 45 minutes (FIG. 4b, lane 1-6). Incubation of these cells with the PKC inhibitor BIS for 1 hr prior to stimulation with LPS prevented the phosphorylation of TRAM (FIG. 4b, lane 7-12). Immunoblotting of lysates from PKCε$^{-/-}$ MEFs reconstituted with PKCε, treated with LPS for 15 and 30 minutes, revealed a band of the correct molecular weight as TRAM (FIG. 4c, top panel, lane 9 and 10). The phosphorylation occurred earlier in this cell type than the THP1 cells as the effect was waning by 45 minutes (lane 11) and was not evident at 60 minutes (lane 12). Levels of total TRAM were not altered in the lysates over the time course (FIG. 4c, second panel). Importantly no band was detected in lysates generated from PKCε$^{-/-}$ MEFs (FIG. 4c, top panel, lane 1-6) and no bands were detected in TRAM-deficient cells attesting to the specificity of the antibody (data not shown). Finally treatment of PKCε expressing MEFs with the TLR2 ligand MALP2 or the TLR3 ligand polyI:C for 30 minutes had no effect (FIG. 4d).

Tram and PKCε are Both Essential for Complete LPS Signaling

Figure 5:
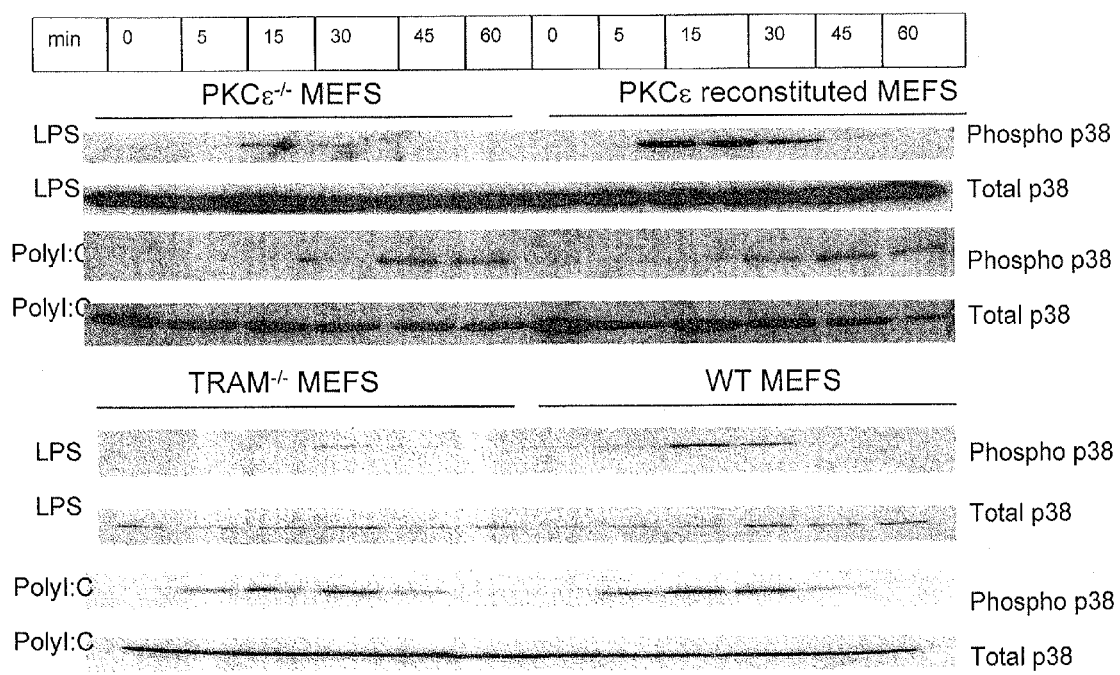
FIG. 5 shows that TRAM and PKCε are both essential for complete LPS signaling. (a) Cells from PKCε$^{-/-}$ MEFs and PKCε$^{-/-}$ MEFs that had been reconstituted with PKCε (top four panels) or TRAM$^{-/-}$ MEFs and WT MEFs (bottom four panels) were stimulated for the indicated times with 1 μg/ml LPS or 5 μg/ml PolyI:C and the lysates were immunoblotted for phosphorylated (Tyr 180/182) and total p38. (b)—PKCε$^{-/-}$ MEFs and PKCε$^{-/-}$ MEFs that had been reconstituted with PKCε were treated with 1 μg/ml LPS or 5 μg/ml polyI:C for the indicated times, run on a non-reducing PAGE gel and immunoblotted for IRF3. (c) The ISRE luciferase reporter gene and the control Renilla luciferase reporter gene were transfected into the above cell types. 24 hours post-transfection the cells were stimulated with 1 μg/ml LPS or 5 μg/ml PolyI:C for 6 hours. The data represents mean fold stimulation of luciferase activity relative to control levels. (d), (e) The above cell types were stimulated with the indicated concentrations of LPS or PolyI:C for 24 hours and then a RANTES ELISA was performed. Results shown are representative of at least three experiments.

TRAM-dependent signaling in PKCε$^{-/-}$ MEFs was then tested. In both TRAM$^{-/-}$ MEFs and PKCε$^{-/-}$ MEFs the phosphorylation of p38 in cells treated with LPS was significantly reduced in comparison to their corresponding wild-type MEFs (FIG. 5a top panel compare lanes 9-11 to 3-5). Importantly, there was no reduction in p38 phosphorylation in response to polyI:C in PKCε$^{-/-}$ MEFs or TRAM$^{-/-}$ MEFs (FIG. 5a panel 3, compare right and left hand sides). We also tested the activation of IRF3 by LPS as indicated by its dimerisation. IRF3 dimerisation induced by LPS was reduced in PKCε$^{-/-}$ MEF relative to MEFs expressing PKCε (FIG. 5b, compare lane 2 and 3 to lane 4 and 5). There was no reduction in IRF3 dimerisation in PKCε$^{-/-}$ MEF in response to polyI:C (FIG. 5c, compare lane 2 and 3 to lane 4 and 5). As shown by Yamamoto et al. this response was also impaired in TRAM-deficient MEFs in response to LPS but not polyI:C. Activation of an IRF3-linked reporter gene was tested and this was impaired in LPS-treated PKCε$^{-/-}$ MEFs but was normal in polyI:C-treated PKCε$^{-/-}$ MEFs (FIG. 5c, right panel). Similar results were obtained in TRAM-deficient MEFs. Induction of RANTES was then assessed as a readout for the TRAM pathway. In TRAM$^{-/-}$ MEFs the levels of RANTES produced in response to LPS stimulation was dramatically reduced in comparison to the corresponding wild type MEFs (FIG. 5d, left panel). The levels of RANTES production in response to polyI:C was not affected (FIG. 5d, right panel). Importantly, this response was also impaired in PKCε$^{-/-}$ cells. As shown in FIG. 5e (left panel), induction of RANTES by LPS was impaired relative to PKCε expressing cells. There was no difference in the response to polyI:C when both cells types were compared (FIG. 5e, right panel).

As the production of RANTES is a marker associated with the TRAM signalling pathway, the impairment in its production in PKCε$^{-/-}$ cells and TRAM$^{-/-}$ MEFs cells further supports the observation that TRAM must be phosphorylated by protein kinase C epsilon and that this phosphorylation is essential for its function.

TRAMS16A is Unable to Fully Reconstitute Signaling in TRAM-Deficient Cells

The clear impairment in TRAM-dependent responses following LPS treatment in PKCε$^{-/-}$ cells, with the same responses being intact in polyI:C-treated cells, coupled with impaired signaling by TRAMS16A, strongly suggested that TRAM phosphorylation by PKCε is essential for TRAM function. To provide further evidence for this we examined the ability of TRAMS16A to reconstitute signaling in TRAM-deficient MEFs. Treatment of wild type MEFs with LPS, induced RANTES production while treatment of TRAM$^{-/-}$ MEFs with LPS caused little or no induction of RANTES production (FIG. 6a). The response of the TRAM-deficient cells could be reconstituted with wild type TRAM. Significantly, TRAMS16A was less capable of reconstituting the signal however Similarly, the phosphorylation of p38 in TRAM-deficient cells upon LPS stimulation was reconstituted with overexpression of WT TRAM. TRAMS16A could not reconstitute this signal (FIG. 6b). It is therefore concluded that phosphorylation of Serine 16 by protein kinase C epsilon must be required for TRAM to function normally upon LPS stimulation.

Levels of TRAM in the Membrane are Reduced Upon LPS Stimulation

The myristoylation of TRAM promotes membrane localization. It is known that certain myristoylated proteins dissociate from the membrane upon phosphorylation. It was further investigated whether phosphorylation of TRAM by PKCε would cause a redistribution of TRAM.

FLAG-TRAM/pcDNA3.1 was transfected into HEK293-TLR4 cells and these cells were then stimulated with or without LPS for 30 minutes. The cells were fractionated into membrane and cytosolic fractions. The amount of TRAM present in the membrane fraction was decreased upon LPS stimulation suggesting that TRAM is disappearing from the membrane (FIG. 7a, top panel compare lane 3 to lane 1). TRAM could not be detected in the cytosolic fraction. This was not due to degradation, since the levels of TRAM in the cell lysates remained constant (FIG. 7a, third panel). The depletion of TRAM from the membrane was PKCε dependent, since the addition of the PKC inhibitor BIS 1 hour prior to LPS stimulation caused FLAG-TRAM to remain in the membrane even after LPS stimulation (FIG. 7a, lane 7).

When tested for depletion of TRAMS16A, no depletion from the membrane was observed (FIG. 7a, second panel). Depletion of endogenous TRAM in THP1 cells treated with LPS (FIG. 7b) was also detected. Finally, in PKCε$^{-/-}$ MEFs FLAG-TRAM did not become depleted from the membrane upon LPS stimulation (FIG. 7c). This evidence suggests that the phosphorylation of TRAM on Serine 16 by PKCε is required for TRAM to be depleted from the membrane.

SUMMARY

TRAM acts as a bridging adaptor between TLR4 and Trif and plays a vital role in the signalling cascade activated by LPS. TRAM is myristoylated and this allows it to associate with the plasma membrane. TRAM is also phosphorylated.

In response to LPS, TRAM becomes phosphorylated and this can be measured in-vitro using a kinase assay described here. This phosphorylation is vital for TRAM to function normally and may be involved in an electrostatic switch, allowing TRAM to move out of the membrane.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

References
1. Janeway, C. A., Jr., Medzhitov, R., 2002. *Annu Rev Immunol* 20, 197-216.
2. Dunne A., O'Neill, L. A., 2003a. *Sci STKE* 2003, re3.
3. Doyle, S. et al. (2002) *Immunity* 17, 251-63.
4. Poltorak A. et al. (1998) *Science* 282, 2085-8.
5. Qureshi S. T. et al. (1999) *J Exp Med* 189, 615-25.
6. Takeda K., Takeuchi O. and Akira S. (2002) *J Endotoxin Res* 8, 459-63.
7. Alexopoulou L. et al. (2001) *Nature* 413, 732-8.
8. Hayashi F. et al. (2001) *Nature* 410, 1099-103.
9. Hemmi H. et al. (2000) *Nature* 408, 740-5.
10. Hemmi H. et al. (2002) *Nat Immunol* 3, 196-200.
11. Adachi O. et al. (1998) *Immunity* 9, 143-50.
12. Takeuchi O. et al. (2000) *J Immunol* 164, 554-7.
13. McGettrick A. F. and O'Neill L. A. (2004) *Mol Immunol* 41, 577-82.
14. Fitzgerald, K. A. et al. (2001) *Nature* 413, 78-83.
15. Horng, T. et al. (2001) *Nat Immunol* 2, 835-41.
16. Horng, T. et al. (2002) *Nature* 420, 329-33.
17. Yamamoto, M. et al. (2002) *J Immunol* 169, 6668-72.
18. Oshiumi, H. et al. (2003) *Nat Immunol* 4, 161-7.
19. Yamamoto, M. et al. (2003) *Science* 301, 640-3.
20. Fitzgerald, K. A. et al. (2003) *J Exp Med* 198, 1043-55.
21. Oshiumi, H. et al. (2003) *J Biol Chem* 278, 49751-49762.
22. Bin, L. H. et al. (2003) *J Biol Chem* 278, 24526-32.
23. Yamamoto, M. et al. (2003) *Nat Immunol* 4, 1144-50.
24. Thelen M. et al. (1991) *Nature* 351, 320-2.
25. Aderem A. A. et al. (1988) *Nature* 332, 362-4.
26. Wu W. C. et al. (1982) *Proc Natl Acad Sci USA* 79, 5249-53.
27. Rozengurt E. et al. (1983) *Proc Natl Acad Sci USA* 80, 7244-8.
28. Rozengurt E. and Sinnett-Smith J. (1983) *Proc Natl Acad Sci USA* 80, 2936-40.
29. Graff J. M. et al. (1989) *Science* 246, 503-6.
30. Rosen A. et al. (1990) *J Exp Med* 172, 1211-5.
31. Matsubara M. et al. (2003) *J Biol Chem* 278, 48898-902.
32. Takasaki A. et al, (1999) *J Biol Chem* 274, 11848-53.
33. Hayashi N., et al. (2000) *Protein Sci* 9, 1905-13.

The invention claimed is:

1. An assay method for determining the activation status of Trif-related adaptor molecule (TRAM), said method comprising the steps of:
    providing a cellular sample comprising TRAM, and
    detecting the phosphorylation of the serine 16 residue of TRAM as an indication of the activation status of TRAM,
wherein the absence of phosphorylation of TRAM at the serine 16 residue indicates that TRAM is not active.

2. The assay method as claimed in claim 1, wherein the phosphorylation of TRAM is detected by measuring the presence or level of TRAM in a cell membrane of the sample.

3. The assay method as claimed in claim 1, further comprising contacting TRAM with protein kinase C epsilon under conditions permissive to the phosphorylation of TRAM.

4. The assay method of claim 2, wherein the presence or level of TRAM in the cell membrane is determined using a membrane depletion assay.

5. A method for identifying modulator(s) of TRAM, said method comprising the steps of:
    (i) providing first and second cellular samples containing TRAM,
    (ii) contacting said first sample with a candidate modulator of TRAM,
    (iii) contacting said first and second samples with a protein kinase C epsilon under conditions permissive of phosphorylation, and
    (iv) monitoring the phosphorylation status of TRAM, and comparing the phosphorylation of TRAM between said first and second samples,
wherein a difference in TRAM phosphorylation between said first and second samples identifies the candidate modulator as a modulator of TRAM activity.

6. The method of claim 5, wherein the phosphorylation of TRAM is determined by measuring the presence or level of TRAM in a cell membrane of the first and second samples, wherein:
    an increase in the presence or level of TRAM in the cell membrane of the first or second sample is indicative of decreased phosphorylation; and a decrease in the presence or level of TRAM in the cell membrane of the first or second sample is indicative of increased phosphorylation.

7. The method of claim 5, wherein the phosphorylation of TRAM is determined by detecting phosphorylation at the serine 16 residue of TRAM.

8. An assay method for the detection of Toll Like receptor 4 (TLR4) activation by a ligand, the assay comprising the steps of:
providing a cellular sample comprising cells expressing the TLR4,
bringing said cells into contact with the ligand, and
detecting the phosphorylation of the serine 16 residue of TRAM,
wherein phosphorylation of TRAM at the serine 16 residue is indicative of the activation of the ligand to TLR4.

9. An assay method as claimed in claim 8, further comprising detecting the phosphorylation of TRAM in a control cellular sample comprising the same type of cells which are not exposed to the ligand, wherein the level of phosphorylation of TRAM detected in the cellular sample exposed to the ligand is compared to the control cellular sample.

10. The assay method of claim 8, wherein the phosphorylation of TRAM is detected by measuring the presence or level of TRAM in a cell membrane of the sample, wherein:
an increase in the presence or level of TRAM in the cell membrane is indicative of decreased phosphorylation; and
a decrease in the presence or level of TRAM in the cell membrane is indicative of increased phosphorylation.

11. The assay method of claim 8, wherein the phosphorylation of TRAM is determined by detecting phosphorylation of TRAM by protein kinase C epsilon.

12. An assay for identifying an agonist of a TLR4 receptor, said assay comprising the steps of:
providing a cellular sample comprising cells which express TLR4,
exposing the cells to a test compound,
detecting the phosphorylation of TRAM,
wherein an increase in the phosphorylation of TRAM is indicative of activation of the TLR4 receptor following binding of the test compound thereto, and
wherein the phosphorylation of TRAM is determined by detecting phosphorylation at the serine 16 residue of TRAM.

13. An assay for identifying an antagonist of a TLR4 receptor, said assay comprising the steps of:
providing a cellular sample comprising cells which express the TLR4,
exposing the cells to a TLR4 agonist,
exposing the cells to a test compound,
detecting the phosphorylation of TRAM,
wherein a decrease in the phosphorylation of TRAM in the presence of a test compound, when compared to the absence of a test compound is indicative of the test compound being an antagonist, and
wherein the phosphorylation of TRAM is determined by detecting phosphorylation at the serine 16 residue of TRAM.

14. The assay according to claim 13, wherein the TLR4 agonist is exposed to the cells prior to exposure to the test compound.

15. An assay method for determining compounds which act as inhibitors of the function of protein kinase C epsilon, the methods comprising the steps of:
providing a candidate compound,
bringing the candidate compound into contact with protein kinase C epsilon,
determining the presence or absence of the ability of protein kinase C epsilon to phosphorylate TRAM,
wherein the absence of phosphorylation of TRAM is indicative of the blocking of the function of protein kinase C epsilon by the candidate compound.

16. An assay for identifying compounds which prevent the phosphorylation of TRAM by protein kinase C epsilon, said assay comprising the steps of:
providing a candidate compound,
bringing the candidate compound into contact with TRAM,
exposing TRAM to protein kinase C epsilon in conditions suitable for phosphorylation to occur, and
determining the presence or absence of phosphorylation of TRAM,
wherein the absence of phosphorylation is indicative of the blocking of the interaction between protein kinase C epsilon and TRAM.

17. An assay for identifying a compound that prevent the phosphorylation of TRAM by protein kinase C epsilon, said assay comprising the steps of:
providing a candidate compound,
bringing the candidate compound into contact with TRAM,
exposing TRAM to protein kinase C epsilon under conditions suitable for phosphorylation to occur,
determining the presence or absence of phosphorylation of TRAM, and
determining the ability of the candidate compound to bind TRAM at or in the region of the domain corresponding to the serine 16 residue present on TRAM in order to prevent the phosphorylation of that serine residue by protein kinase C epsilon,
wherein the absence of phosphorylation is indicative of the blocking of the interaction between protein kinase C epsilon and TRAM.

18. An assay for identifying an agonist of a TLR4 receptor, said assay comprising:
providing a cellular sample comprising cells which express TLR4,
exposing the cells to a test compound,
detecting the phosphorylation of TRAM,
wherein an increase in the phosphorylation of TRAM is indicative of activation of the TLR4 receptor following binding of the test compound thereto, wherein the phosphorylation of TRAM is detected by measuring the presence or level of TRAM in a cell membrane of the sample, wherein:
an increase in the presence or level of TRAM in the cell membrane is indicative of decreased phosphorylation; and
a decrease in the presence or level of TRAM in the cell membrane is indicative of increased phosphorylation.

19. An assay for identifying an antagonist of a TLR4 receptor, said assay comprising:
providing a cellular sample comprising cells which express the TLR4, —exposing the cells to a TLR4 agonist,
exposing the cells to a test compound,
detecting the phosphorylation of TRAM,
wherein a decrease in the phosphorylation of TRAM in the presence of a test compound, when compared to the absence of a test compound is indicative of the test compound being an antagonist; and wherein the phosphorylation of TRAM is detected by measuring the presence or level of TRAM in a cell membrane of the sample, wherein:
an increase in the presence or level of TRAM in the cell membrane is indicative of decreased phosphorylation; and
a decrease in the presence or level of TRAM in the cell membrane is indicative of increased phosphorylation.

* * * * *